United States Patent
Choi

(10) Patent No.: US 9,907,776 B2
(45) Date of Patent: Mar. 6, 2018

(54) PHENYL CARBAMATE COMPOUND AND A COMPOSITION FOR PREVENTING OR TREATING A PSYCHIATRIC DISORDER COMPRISING THE SAME

(71) Applicant: Bio-Pharm Solutions Co., Ltd., Gyeonggi-do (KR)

(72) Inventor: Yong Moon Choi, Pine Brook, NJ (US)

(73) Assignee: Bio-Pharm Solutions, Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/775,037

(22) PCT Filed: Mar. 12, 2014

(86) PCT No.: PCT/KR2014/002062
§ 371 (c)(1),
(2) Date: Sep. 11, 2015

(87) PCT Pub. No.: WO2014/142550
PCT Pub. Date: Sep. 18, 2014

(65) Prior Publication Data
US 2016/0015678 A1  Jan. 21, 2016

Related U.S. Application Data

(60) Provisional application No. 61/776,926, filed on Mar. 12, 2013.

(30) Foreign Application Priority Data

Jun. 10, 2013  (KR) .................. 10-2013-0065781

(51) Int. Cl.
| A61K 31/27 | (2006.01) |
|---|---|
| A61K 31/166 | (2006.01) |
| A61K 31/325 | (2006.01) |
| C07C 271/12 | (2006.01) |
| C07C 271/24 | (2006.01) |

(52) U.S. Cl.
CPC ............ *A61K 31/27* (2013.01); *A61K 31/166* (2013.01); *A61K 31/325* (2013.01); *C07C 271/12* (2013.01); *C07C 271/24* (2013.01); *C07C 2601/02* (2017.05); *C07C 2601/14* (2017.05); *C07C 2602/42* (2017.05)

(58) Field of Classification Search
CPC .... A61K 31/166; A61K 31/27; A61K 31/325; C07C 2101/02; C07C 2101/14; C07C 2102/42; C07C 271/12; C07C 271/24
See application file for complete search history.

(56) References Cited

U.S. PATENT DOCUMENTS

| 3,313,696 | A | 4/1967 | Bossinger et al. |
|---|---|---|---|
| 5,990,177 | A * | 11/1999 | Brown ................. A61K 31/045 514/724 |
| 6,562,867 | B2 * | 5/2003 | Plata-Salaman ....... A61K 31/27 514/489 |
| 9,624,164 | B2 * | 4/2017 | Choi ....................... C07C 33/26 |
| 9,682,059 | B2 * | 6/2017 | Choi ..................... C07C 271/12 |
| 2008/0317883 | A1 * | 12/2008 | Choi ..................... A61K 45/06 424/730 |

FOREIGN PATENT DOCUMENTS

| KR | 10-2003-0078947 | 10/2003 |
|---|---|---|
| KR | 10-0886578 | 3/2009 |
| KR | 10-2009-0067210 | 6/2009 |
| KR | 10-2009-0082213 | 7/2009 |
| KR | 10-0910928 | 8/2009 |
| KR | 10-2009-0110889 | 10/2009 |
| WO | 2002/067925 A1 | 6/2002 |
| WO | 2002051395 A1 | 7/2002 |
| WO | 2012/096458 A2 | 7/2012 |

OTHER PUBLICATIONS

International Search Report dated Jun. 24, 2014 for PCT International Application No. PCT/KR2014/002062 filed Mar. 12, 2014.

* cited by examiner

*Primary Examiner* — Sreeni Padmanabhan
*Assistant Examiner* — Jody Karol
(74) *Attorney, Agent, or Firm* — McDonnell Boehnen Hulbert & Berghoff LLP

(57) ABSTRACT

The present invention relates to a composition for preventing or treating a psychiatric disorder comprising a phenyl carbamate compound and a method for preventing or treating a psychiatric disorder therewith. The present invention provides anti-anxiety activity and protections against seizure and bipolar disorder, such that it may be effectively used for preventing or treating various psychiatric disorders related to mood disorder or resulting convulsion.

6 Claims, No Drawings

PHENYL CARBAMATE COMPOUND AND A COMPOSITION FOR PREVENTING OR TREATING A PSYCHIATRIC DISORDER COMPRISING THE SAME

CROSS-REFERENCE TO RELATED APPLICATIONS

This application is a US national phase application of International Patent Application No. PCT/KR2014/002062 filed on 12 Mar. 2014, which claims the benefit of the filing date of U.S. Provisional Application Ser. No. 61/776,926 filed 12 Mar. 2013, and of Korean Application Serial No. 10-2013-0065781, filed 10 Jun. 2013.

BACKGROUND OF THE INVENTION

Field of the Invention

The present invention relates to a composition for preventing or treating a psychiatric disorder comprising a phenyl carbamate compound and a method for preventing or treating a psychiatric disorder therewith.

Description of the Related Art

Psychiatry is the medical specialty devoted to the study, diagnosis, treatment, and prevention of mental disorders. These include various affective, behavioural, cognitive and perceptual abnormalities. A number of psychiatric syndromes feature depressed mood as a main symptom. Depression is a state of low mood and aversion to activity that can affect a person's thoughts, behavior, feelings and sense of well-being. Depressed people may feel sad, anxious, empty, hopeless, worried, helpless, worthless, guilty, irritable, hurt, or restless. The mood disorders are a group of disorders considered to be primary disturbances of mood. These include major depressive disorder (MDD; commonly called major depression or clinical depression) where a person has at least two weeks of depressed mood or a loss of interest or pleasure in nearly all activities; and dysthymia, a state of chronic depressed mood, the symptoms of which do not meet the severity of a major depressive episode.

Another mood disorder, bipolar disorder, features one or more episodes of abnormally elevated mood, cognition and energy levels, but may also involve one or more depressive episodes. When the course of depressive episodes follows a seasonal pattern, the disorder (major depressive disorder, bipolar disorder, etc.) may be described as a seasonal affective disorder. Outside the mood disorders: borderline personality disorder commonly features depressed mood; adjustment disorder with depressed mood is a mood disturbance appearing as a psychological response to an identifiable event or stressor, in which the resulting emotional or behavioral symptoms are significant but do not meet the criteria for a major depressive episode and posttraumatic stress disorder, an anxiety disorder that sometimes follows trauma, is commonly accompanied by depressed mood. Bipolar disorder has been known for decades as a chronic mental disorder, with high relapse rates, most of times incapacitating, supposedly having a neurobiological substrate. Although the understanding of neurobiology has expanded in the last years, little is known about the real pathophysiological mechanisms of bipolar disorder. One of the models that has been applied to bipolar disorder is kindling, taken from the model of epilepsy, in which the repetition of crises would cause a process of neuronal sensitization, leading to a progressive threshold decrease, with the increase in the recurrence of epileptic crises (manic). Animal model studies suggest that this process may involve a series of alterations in the genic expression and second messengers In fact, pharmacological studies have been consistent with these findings, demonstrating the action of antidepressants and mood stabilizers in several intracellular mechanisms which involve the regulation of genic expression and cellular plasticity (Benicio Noronha Frey et al., Rev Bras Pisquiatr 2004; 26(3):180-8).

Anxiety is an unpleasant state of inner turmoil, often accompanied by nervous behavior, such as pacing back and forth, somatic complaints and rumination. It is the subjectively unpleasant feelings of dread over something unlikely to happen, such as the feeling of imminent death. Pentylenetetrazol (PTZ), a GABA(A) receptor antagonist and prototypical anxiogenic drug, has been extensively utilized in animal models of anxiety. PTZ produces a reliable discriminative stimulus which is largely mediated by the GABA(A) receptor (Jung M E et al., Neurosci Biobehav Rev. 2002 June; 26(4):429-39). Anxiety is not the same as fear, which is felt about something realistically intimidating or dangerous and is an appropriate response to a perceived threat. Anxiety is a mood. When it becomes a mental disorder, that is, characterized by excessive, uncontrollable and often irrational worry about everyday things that is disproportionate to the actual source of worry, it is diagnosed as generalized anxiety disorder (GAD). GAD occurs without an identifiable triggering stimulus. It is called generalized because the remorseless worries are not focused on any specific threat; they are, in fact, often exaggerated and irrational. Subtypes of anxiety disorders are phobias, social anxiety, obsessive-compulsive behavior, and Posttraumatic stress disorder Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventor has made intensive studies to develop a novel agent exhibiting excellent treating activity for psychiatric disorders related to mood disorder, as well as resulting physical symptoms. As results, the present inventor has discovered that the phenyl carbamate derivatives represented by above formula 1 provide highly enhanced anti-anxiety activity and protections against seizure and bipolar disorder.

Accordingly, it is an object of this invention to provide a composition for preventing or treating a psychiatric disorder.

It is another object of this invention to provide a method for preventing or treating a psychiatric disorder.

Other objects and advantages of the present invention will become apparent from the following detailed description together with the appended claims and drawings.

DETAILED DESCRIPTION OF THE INVENTION

In one aspect of this invention, there is provided a composition for preventing or treating a psychiatric disorder selected from the group consisting of depressive disorder, bipolar disorder, anxiety disorder and seizure comprising a compound represented by the following formula 1 or pharmaceutically acceptable salt thereof as an active ingredient:

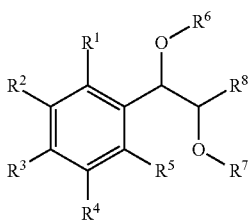

(1)

wherein $R^1$, $R^2$, $R^3$, $R^4$ and $R^5$ are each independently selected from the group consisting of hydrogen, and halogen; $R^6$ and $R^7$ are each independently hydrogen or

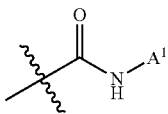

($A^1$ is selected from the group consisting of hydrogen, $C_1$-$C_5$ alkyl, $C_3$-$C_8$ cycloalkyl, $C_6$-$C_{10}$ aryl $C_1$-$C_3$ alkyl and bridged $C_6$-$C_8$ bicycloalkane) wherein one of $R^6$ and $R^7$ is hydrogen; and $R^8$ is $C_1$-$C_5$ alkyl.

The present inventor has made intensive studies to develop a novel agent exhibiting excellent treating activity for psychiatric disorders related to mood disorder, as well as resulting physical symptoms. As results, the present inventor has discovered that the phenyl carbamate derivatives represented by above formula 1 provide highly enhanced anti-anxiety activity and protections against seizure and bipolar disorder.

The term "psychiatric disorder" as used herein, refers to a condition with mental or behavioral pattern or anomaly that causes distress or disability, and which is not developmentally or socially normative. As used herein, "psychiatric disorder" is used interchangeably with "mental disorder".

The term "depressive disorder" as used herein, refers to a mental disorder with a pervasive and persistent low mood. The depressive disorder referred in the present invention includes major depressive disorder (MDD) in which a patient has at least two weeks of depressed mood or a loss of interest in almost every activities, and dysthymia that shows a chronic depressed mood, of which the symptom is less severe than MDD.

The term "bipolar disorder" as used herein, refers to a mental disorder which involves episodes of an elevated or agitated mood known as mania alternating with episodes of depression.

The term "anxiety disorder" as used herein, refers to a mental disorder characterized by excessive rumination, worrying, fear, uneasiness and apprehension about future uncertainties either based on real or imagined events.

The term "seizure" as used herein, refers to brief episodes of abnormal excessive or synchronous neuronal activity in the brain. The seizure referred in the present invention includes epileptic seizures, non-epileptic seizures, focal seizures and generalized seizures.

The term "alkyl" as used herein, refers to a straight or branched chain of saturated hydrocarbon group, e.g., methyl, ethyl, propyl, butyl, isobutyl, tert butyl and pentyl. "$C_1$-$C_5$ alkyl group" as used herein, refers to an alkyl group with carbon number of 1-5.

The term "aryl" as used herein, refers to a totally or partially unsaturated monocylic or polycyclic carbon rings having aromaticity. The aryl group of the present invention is preferably monoaryl or biaryl.

The term "bridged bicycloalkane" as used herein, refers to a cycloalkane containing two rings and two bridgehead carbon atoms shared by all three rings identifiable in the molecule.

According to a concrete embodiment, $R^1$, $R^2$, $R^3$, $R^4$ and $R^5$ are each independently selected from the group consisting of hydrogen, chlorine, fluorine and iodine. More concretely, $R^1$, $R^2$, $R^3$, $R^4$ and $R^5$ are not hydrogen at the same time.

According to a concrete embodiment, $R^6$ and $R^7$ are each independently hydrogen or

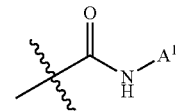

($A^1$ is selected from the group consisting of hydrogen, $C_1$-$C_4$ alkyl, cyclopropyl, cyclohexyl, phenyl $C_1$-$C_3$ alkyl and bicycloheptane).

According to a concrete embodiment, $R^6$ and $R^7$ are each independently hydrogen or

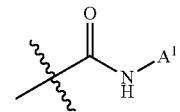

($A^1$ is selected from the group consisting of hydrogen, $C_1$-$C_4$ alkyl, cyclopropyl, cyclohexyl, benzyl and bicycle[2.2.1] heptane), and wherein one of R6 and R7 is hydrogen.

According to more concrete embodiment, the compound is selected from the group consisting of:
(1) 1-(2-chlorophenyl)-1-hydroxypropyl-2-carbamate;
(2) 1-(2-chlorophenyl)-1-hydroxybutyl-2-carbamate;
(3) 1-(2-chlorophenyl)-1-hydroxy-3-methyl-butyl-2-carbamate;
(4) 1-(2-chlorophenyl)-1-hydroxyhexyl-2-carbamate;
(5) 1-(2-chlorophenyl)-1-hydroxypropyl-2-N-methylcarbamate;
(6) 1-(2-chlorophenyl)-1-hydroxypropyl-2-N-propylcarbamate;
(7) 1-(2-chlorophenyl)-1-hydroxpropyl-2-N-isopropylcarbamate;
(8) 1-(2-chlorophenyl)-1-hydroxpropyl-2-N-cyclopropylcarbamate;
(9) 1-(2-chlorophenyl)-1-hydroxypropyl-2-N-cyclohexylcarbamate;
(10) 1-(2-chlorophenyl)-1-hydroxypropyl-2-N-benzylcarbamate;
(11) 1-(2-chlorophenyl)-1-hydroxypropyl-2-N-bicyclo[2,2,1]heptanecarbamate;
(12) 1-(2,4-dichlorophenyl)-1-hydroxypropyl-2-carbamate;
(13) 1-(2,6-dichlorophenyl)-1-hydroxypropyl-2-carbamate;
(14) 1-(2,4-dichlorophenyl)-1-hydroxybutyl-2-carbamate;
(15) 1-(2,6-dichlorophenyl)-1-hydroxybutyl-2-carbamat;
(16) 1-(2,4-dichlorophenyl)-1-hydroxy-3-methyl-butyl-2-carbamate;

(17) 1-(2,6-dichlorophenyl)-1-hydroxy-3-methyl-butyl-2-carbamate;
(18) 1-(2,4-dichlorophenyl)-1-hydroxyhexyl-2-carbamate;
(19) 1-(2,6-dichlorophenyl)-1-hydroxyhexyl-2-carbamate;
(20) 1-(2-chlorophenyl)-2-hydroxypropyl-1-carbamate;
(21) 1-(2-chlorophenyl)-2-hydroxypropyl-1-N-methylcarbamate;
(22) 1-(2-chlorophenyl)-2-hydroxypropyl-1-N-propylcarbamate;
(23) 1-(2-chlorophenyl)-2-hydroxypropyl-1-N-isopropylcarbamate;
(24) 1-(2-chlorophenyl)-2-hydroxypropyl-1-N-cyclopropylcarbamate;
(25) 1-(2-chlorophenyl)-2-hydroxypropyl-1-N-cyclohexylcarbamate;
(26) 1-(2-chlorophenyl)-2-hydroxypropyl-1-N-benzylcarbamate;
(27) 1-(2,4-dichlorophenyl)-2-hydroxypropyl-1-carbamate;
(28) 1-(2,6-dichlorophenyl)-2-hydroxypropyl-1-carbamate;
(29) 1-(2,4-dichlorophenyl)-2-hydroxybutyl-1-carbamate;
(30) 1-(2,6-dichlorophenyl)-2-hydroxybutyl-1-carbamate;
(31) 1-(2,4-dichlorophenyl)-2-hydroxy-3-methyl-butyl-1-carbamate;
(32) 1-(2,6-dichlorophenyl)-2-hydroxy-3-methyl-butyl-1-carbamate;
(33) 1-(2,4-dichlorophenyl)-2-hydroxyhexyl-1-carbamate;
(34) 1-(2,6-dichlorophenyl)-2-hydroxyhexyl-1-carbamate;
(35) 1-(2-fluorophenyl)-1-hydroxypropyl-2-carbamate;
(36) 1-(2-iodophenyl)-1-hydroxypropyl-2-carbamate;
(37) 1-(2-iodophenyl)-1-hydroxybutyl-2-carbamate;
(38) 1-(2,3-dichlorophenyl)-1-hydroxypropyl-2-carbamate; and
(39) 1-(2,3-dichlorophenyl)-1-hydroxypropyl-1-carbamate.

According to even more concrete embodiment, the compound is selected from the group consisting of:
(1) 1-(2-chlorophenyl)-1-hydroxypropyl-2-carbamate;
(2) 1-(2-chlorophenyl)-1-hydroxybutyl-2-carbamate;
(4) 1-(2-chlorophenyl)-1-hydroxyhexyl-2-carbamate;
(6) 1-(2-chlorophenyl)-1-hydroxypropyl-2-N-propylcarbamate;
(8) 1-(2-chlorophenyl)-1-hydroxypropyl-2-N-cyclopropylcarbamate;
(12) 1-(2,4-dichlorophenyl)-1-hydroxypropyl-2-carbamate;
(13) 1-(2,6-dichlorophenyl)-1-hydroxypropyl-2-carbamate;
(14) 1-(2,4-dichlorophenyl)-1-hydroxybutyl-2-carbamate;
(17) 1-(2,6-dichlorophenyl)-1-hydroxy-3-methyl-butyl-2-carbamate;
(35) 1-(2-fluorophenyl)-1-hydroxypropyl-2-carbamate;
(36) 1-(2-iodophenyl)-1-hydroxypropyl-2-carbamate;
(37) 1-(2-iodophenyl)-1-hydroxybutyl-2-carbamate; and
(38) 1-(2,3-dichlorophenyl)-1-hydroxypropyl-2-carbamate.

According to concrete embodiment, the compound is in the form of racemate, enantiomer, diastereomer, a mixture of enantiomer or a mixture of diastereomer.

In this compound, 2 chiral carbons exist at positions 1 and 2 from phenyl group; thus, the compound may exist in the form of an enantiomer, a diastereomer, a mixture of enantiomers, or a mixture of diastereomers, as well as a racemate.

According to more concrete embodiment, the racemate, enantiomer, diastereomer, mixture of enantiomer or mixture of diastereomer of the compound above described is selected from the group consisting of:
1-(2-chlorophenyl)-(S)-1-hydroxypropyl-(S)-2-carbamate,
1-(2-chlorophenyl)-(R)-1-hydroxypropyl-(R)-2-carbamate,
racemate of 1-(2-chlorophenyl)-(S)-1-hydroxypropyl-(S)-2-carbamate and 1-(2-chlorophenyl)-(R)-1-hydropropyl-(R)-2-carbamate,
1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxybutyl-(S)-2-carbamate,
racemate of 1-(2-chlorophenyl)-(S)-1-hydroxybutyl-(S)-2-carbamate and 1-(2-chlorophenyl)-(R)-1-hydroxybutyl-(R)-2-carbamate,
1-(2-chlorophenyl)-(S)-1-hydroxy-3-methyl-butyl-(S)-2-carbamate,
racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(R)-2-N-isopropylcarbamate,
1-(2-chlorophenyl)-(S)-1-hydroxypropyl-(R)-2-N-cyclopropylcarbamate,
1-(2-chlorophenyl)-(S)-1-hydroxypropyl-(R)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxpropyl-(R)-2-N-cyclopropylcarbamate,
1-(2-chlorophenyl)-(R)-1-hydroxypropyl-(R)-2-N-cyclohexyl carbamate,
racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate
racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
racemate of 1-(2-chlorophenyl)-(S)-1-hydroxypropyl-(S)-2-N-isopropylcarbamate and 1-(2-chlorophenyl)-(R)-1-hydroxpropyl-(R)-2-N-isopropylcarbamate,
racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxpropyl-(R)-2-carbamate, and
1-(2-iodophenyl)-(S)-1-hydroxybutyl-(S)-2-carbamate.

As seen in the Examples, the present inventors have synthesized the compounds of various stereochemistries, and investigated their neuroprotecting activity by multilateral experiments.

The term "enantiomer" as used herein, refers to one of two stereoisomers that are mirror images of each other which are non-superposable due to existence of one or more chiral carbons. According to a concrete embodiment, the enantiomer of the present invention is one in which chiral carbons of C1 and C2 are diverse in stereo-configuration.

The term "diastereomer" as used herein, refers to stereoisomers that are not enantiomers, which occurs when two or more stereoisomers of a compound have different configurations at one or more (but not all) of the equivalent chiral centers thus are not mirror images of each other.

The term "racemate" as used herein, refers to one that has equal amounts of two enantiomers of different stereo-configuration, and lack in optical activity.

It would be obvious to the skilled artisan from the Examples below that the compounds of this invention are not limited to those with specific stereochemistry.

According to concrete embodiment, the pharmaceutically acceptable salt is produced by reacting the compound with an inorganic acid, an organic acid, an amino acid, sulfonic acid, an alkali metal or ammonium ion.

The pharmaceutically acceptable salts of the present invention are those which can be manufactured by using a method known in the art, for example, but not limited to, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, and proline; salts with sulfonic acid such as methane sulfonate, ethane sulfonate, benzene sulfonate and toluene sulfonate; metal salts by reaction with an alkali metal such as sodium and potassium; or salts with ammonium ion.

In another aspect of this invention, there is provided a method for preventing or treating a psychiatric disorder selected from the group consisting of depressive disorder, bipolar disorder, anxiety disorder and seizure comprising administering a pharmaceutically effective amount of the composition of the present invention to a subject in need thereof.

As discussed, the present inventor has observed that administration of the instant compound provide anti-anxiety activity and protections against seizure and bipolar disorder, suggesting that the compound of the present invention may be used for effective agent for treating psychiatric disorder related to mood disorder or resulting convulsion.

As the common descriptions regarding the compound of this invention and the diseases prevented or treated thereby are mentioned above, they are omitted herein to avoid excessive overlaps.

The composition of this invention may be provided as a pharmaceutical composition comprising a pharmaceutically effective amount of the compound or pharmaceutically acceptable salt thereof.

The term "pharmaceutically effective amount" as used herein, refers to an amount enough to show and accomplish efficacies and activities for preventing, alleviating, treating a psychiatric disorder.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995).

The pharmaceutical composition according to the present invention may be administered orally or parenterally, and concretely, administered parenterally. For parenteral administration, it may be administered intravenously, subcutaneously, intramuscularly, intraperitoneally, transdermally or intra-articularly. More concretely, it is administered intramuscularly or intraperitoneally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

The present invention will now be described in further detail by examples. It would be obvious to those skilled in the art that these examples are intended to be more concretely illustrative and the scope of the present invention as set forth in the appended claims is not limited to or by the examples.

EXAMPLES

[Reaction Formula I] Synthesis of Diol-1

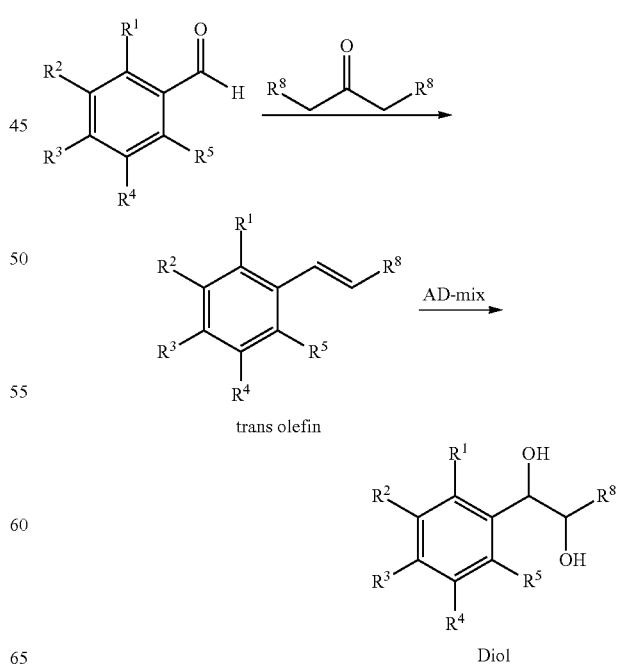

trans olefin

Diol

A diol compound used in the synthesis of the carbamate compound may be synthesized by dihydroxylation of a trans-olefin compound. A diol compound having optical activity may be synthesized using a sharpless asymmetric dihydroxylation catalyst.

[Reaction Formula II] Synthesis of Diol-2

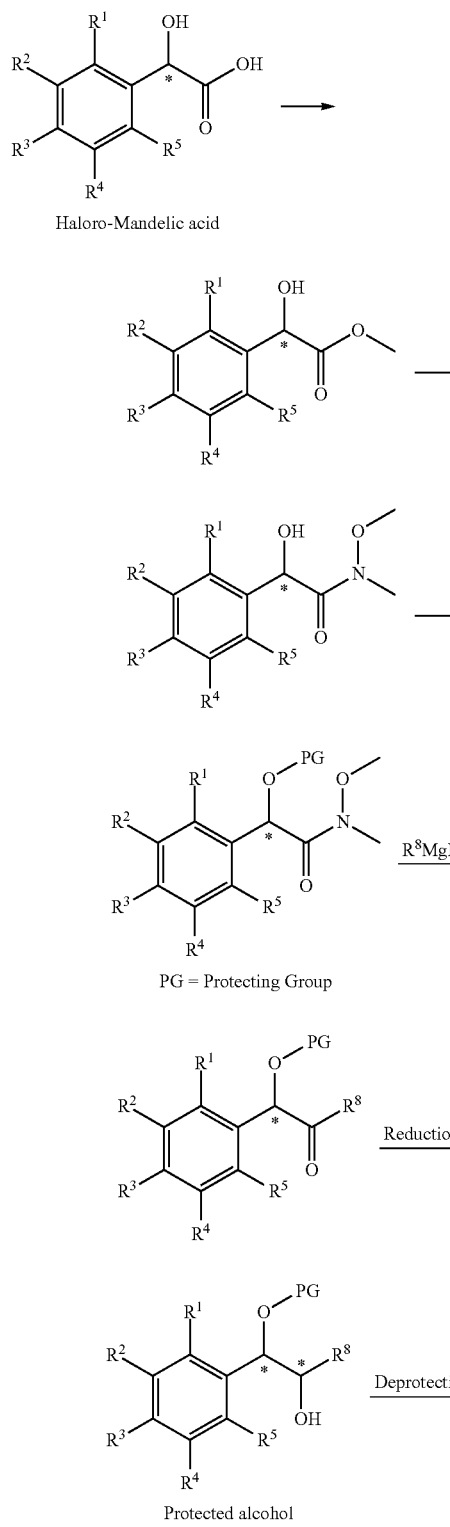

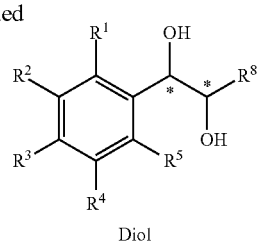

Diol

As indicated in the Reaction Formula II, the optically active substance of diol may also be synthesized using a reduction reagent after synthesizing a hydroxy-ketone compound using Haloro-Mandelic acid. In the Reaction Formula II, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic $C_1$-$C_4$ alkyl groups, and each aryl group may be independently selected from the group consisting of $C_5$-$C_8$ aryl groups, preferably a phenyl group.

[Reaction Formula III] Carbamation Reaction-1

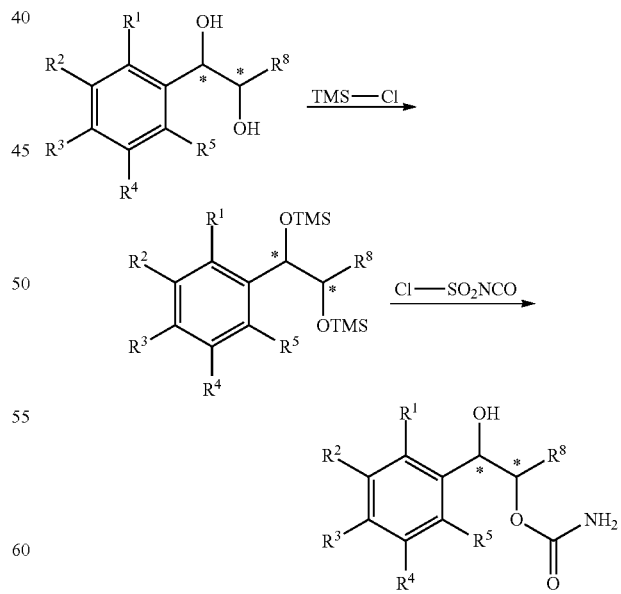

A highly selectivity form of regioisomer of single carbamate of diol having halogen substituent at phenyl ring is prepared (Example 1~14 and 36~67 are synthesized by reaction formula III).

[Reaction Formula IV] Carbamation Reaction-2

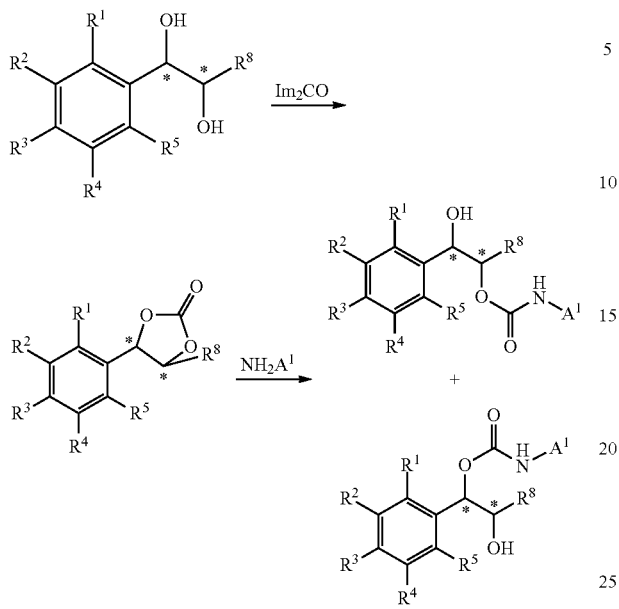

Two substances in the form of regioisomers of a single carbamate of diol having halogen substituent at phenyl ring may be separated by flash column chromatography to obtain two kinds of single carbamate compounds. (Example 15~35 and 68~115 are synthesized by reaction formula IV)

[Reaction Formula V] Protection Reaction

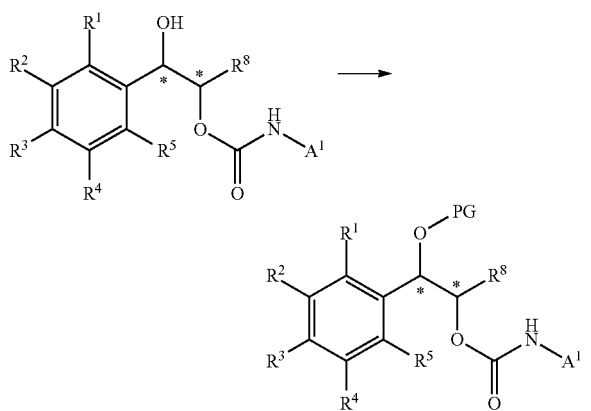

In the Reaction Formula V, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic $C_1$-$C_4$ alkyl groups, and each aryl group may be independently selected from the group consisting of $C_5$-$C_8$ aryl groups, preferably a phenyl group.

In the Reaction Formula IV and V, $A^1$ is selected from the group consisting of hydrogen, $C_1$-$C_5$ alkyl, $C_3$-$C_7$ cycloalkyl, $C_6$-$C_{10}$ aryl $C_1$-$C_3$ alkyl and bridged $C_6$-$C_8$ bicycloalkane. Two substances in the form of regioisomers of a single carbamate of diol having halogen substituent at phenyl ring may be separated by flash column chromatography to obtain two kinds of single carbamate compounds.

Preparation Example 1: Synthesis of 1-(2-chlorophenyl)-trans-1-propene

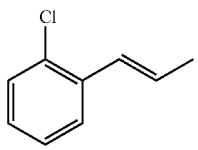

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%).

$^1$H NMR (400 MHz, $CDCl_3$) δ1.94 (d, J=4.8 Hz, 3H), 6.24 (m, 1H), 6.78 (d, J=14 Hz, 1H), 7.11~7.51 (m, 4H)

Preparation Example 2: Synthesis of 1-(2-chlorophenyl)-trans-1-butene

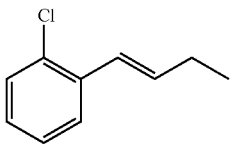

The substantially same method as described in Preparation Example 1 was conducted, except that 3-heptanone was used instead of 3-pentanone, to obtain the title compound (2.9 g, yield 83%).

$^1$H NMR (400 MHz, $CDCl_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.13~7.54 (m, 4H)

Preparation Example 3: Synthesis of 1-(2-chlorophenyl)-3-methyl-trans-1-butene

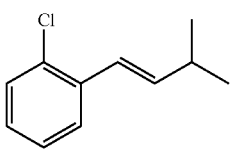

The substantially same method as described in Preparation Example 1 was conducted, except that 2,6-dimethyl-heptan-4-one was used instead of 3-pentanone, to obtain the title compound (8.0 g, yield 50~90%).

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.12~7.54 (m, 4H)

Preparation Example 4: Synthesis of 1-(2-chlorophenyl)-trans-1-hexene

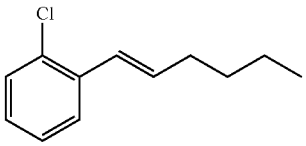

The substantially same method as described in Preparation Example 1 was conducted, except that 6-undecanone was used instead of 3-pentanone, to obtain the title compound (10 g, yield 85%).

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.13~7.54 (m, 4H)

Preparation Example 5: Synthesis of 1-(2,4-dichlorophenyl)-trans-1-propene

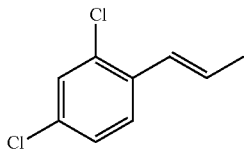

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 6: Synthesis of 1-(2,4-dichlorophenyl)-trans-1-butene

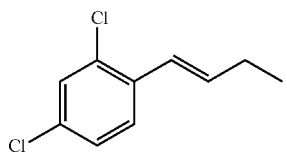

The substantially same method as described in Preparation Example 5 was conducted, except that 3-heptanone was used instead of 3-pentanone, to obtain the title compound (2.1 g, yield 90%).

$^1$H NMR (400 MHz, CDCl$_3$) δ1.14 (d, J=7.6 Hz, 3H), 2.20~2.33 (m, 2H), 6.26 (dt, J=16 Hz, 6.8 Hz, 1H), 6.70 (d, J=15.6 Hz, 1H), 7.18~7.46 (m, 3H)

Preparation Example 7: Synthesis of 1-(2,6-dichlorophenyl)-3-methyl-trans-1-butene

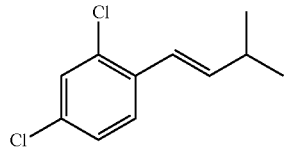

The substantially same method as described in Preparation Example 5 was conducted, except that 2,6-dimethyl-heptan-4-one was used instead of 3-pentanone, to obtain the title compound (0.23 g, yield 10~40%).

$^1$H NMR (400 MHz, CDCl$_3$) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.18~7.46 (m, 3H)

Preparation Example 8: Synthesis of 1-(2,4-dichlorophenyl)-trans-1-hexene

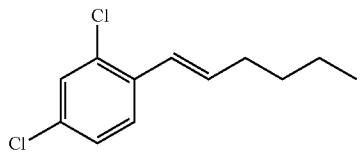

The substantially same method as described in Preparation Example 5 was conducted, except that 6-undecanone was used instead of 3-pentanone, to obtain the title compound (3.2 g, yield 40~80%).

$^1$H NMR (400 MHz, CDCl$_3$) δ0.96 (t, J=7.2 Hz, 3H), 1.38~1.52 (m, 4H), 2.25~2.31 (m, 2H), 6.22 (dt, J=15.6 Hz, 6.8 Hz, 1H), 6.70 (d, J=15.6 Hz, 1H), 7.18~7.46 (m, 3H)

Preparation Example 9: Synthesis of 1-(2,6-dichlorophenyl)-trans-1-propene

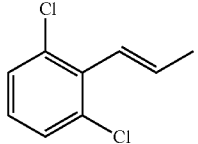

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR (400 MHz, CDCl$_3$) δ1.98 (d, J=8 Hz, 3H), 6.23~6.31 (m, 1H), 6.40 (d, J=16 Hz, 1H), 7.05~7.32 (m, 3H)

Preparation Example 10: Synthesis of 1-(2,6-dichlorophenyl)-trans-1-butene

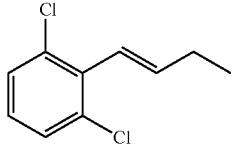

The substantially same method as described in Preparation Example 9 was conducted, except that 3-heptanone was used instead of 3-pentanone, to obtain the title compound (1.2 g, yield 10~40%).

$^1$H NMR (400 MHz, CDCl$_3$) δ1.17 (t, J=7.6 Hz, 3H), 2.30~2.37 (m, 2H), 6.29 (dt, J=16.4 Hz, 6 Hz, 1H), 6.37 (d, J=16.4 Hz, 1H), 7.05~7.32 (m, 3H)

Preparation Example 11: Synthesis of 1-(2,6-dichlorophenyl)-3-methyl-trans-1-butene

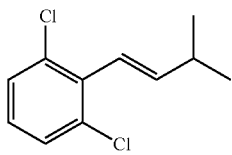

The substantially same method as described in Preparation Example 9 was conducted, except that 2,6-dimethylheptan-4-one was used instead of 3-pentanone, to obtain the title compound (0.23 g, yield 10~40%).

$^1$H NMR (400 MHz, CDCl$_3$) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.05~7.32 (m, 3H)

Preparation Example 12: Synthesis of 1-(2,6-dichlorophenyl)-trans-1-hexene

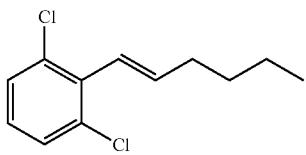

The substantially same method as described in Preparation Example 9 was conducted, except that 6-undecanone was used instead of 3-pentanone, to obtain the title compound (0.2 g, yield 10~40%).

$^1$H NMR (400 MHz, CDCl$_3$) δ0.99 (t, J=7.2 Hz, 3H), 1.14~1.59 (m, 4H), 2.30~2.36 (m, 2H), 6.24 (dt, J=16 Hz, 6.6 Hz, 1H), 6.38 (d, J=16.4 Hz, 1H), 7.05~7.33 (m, 3H)

Preparation Example 13: Synthesis of 1-(2,3-dichlorophenyl)-trans-1-propene

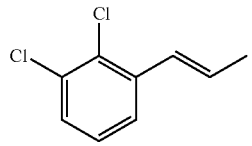

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^1$H NMR (400 MHz, CDCl$_3$) δ1.94 (d, J=4.8 Hz, 3H), 6.24 (m, 1H), 6.78 (d, J=14 Hz, 1H), 7.11~7.51 (m, 3H)

Preparation Example 14: Synthesis of 1-(2-chlorophenyl)-(S,S)-1,2-propanediol

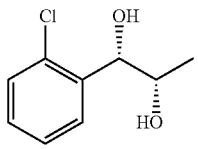

1-(2-chlorophenyl)-trans-1-propene (1.5 g, Preparation Example 1) was dissolved in 30 mL of the mixture of t-BuOH/H$_2$O (1:1 (V/V)). At 0° C., AD-mix-α (Aldrich, U.S.A.) (13.7 g) and methane sulfone amide (CH$_3$SO$_2$NH$_2$, 0.76 g, 0.0080 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (1.65 g, yield 90%).

$^1$H NMR (400 MHz, CDCl$_3$) δ1.20 (d, J=6.4 Hz, 3H), 2.48 (d, J=4.0 Hz 1H), 2.92 (d, J=4.4 Hz, 1H), 3.93~3.97 (m, 1H), 4.97 (t, J=4.8 Hz, 1H), 7.22~7.51 (m, 4H)

$^{13}$C NMR (100 MHz, CDCl$_3$) δ18.8, 71.5, 74.4, 127.1, 128.1, 128.9, 129.5, 132.6, 138.9

Preparation Example 15: Synthesis of 1-(2-chlorophenyl)-(R,R)-1,2-propanediol

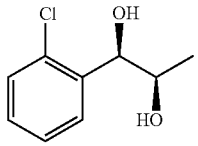

1-(2-chlorophenyl)-trans-1-propene (2.5 g, Preparation Example 1) was dissolved in 50 mL of the mixture of t-BuOH/H$_2$O (1:1 (V/V)). At 0° C., AD-mix-α (Aldrich, U.S.A.) (23.5 g) and methane sulfone amide (CH$_3$SO$_2$NH$_2$, 1.27 g, 0.013 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concentrated under reduced pressure. The concentrated residue was purified by a silica gel column chromatography to produce the title compound (2.96 g, yield 90%).

¹H NMR (400 MHz, CDCl₃) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 16: Synthesis of the Mixture of 1-(2-chlorophenyl)-(S,S)-1,2-propanediol and 1-(2-chlorophenyl)-(R,R)-1,2-propanediol

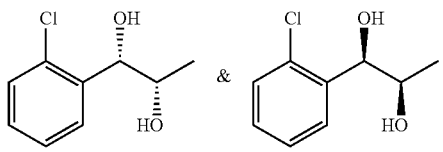

1-(2-chlorophenyl)-trans-1-propene (6.53 g, Preparation Example 1) was dissolved in 45 mL of the mixture of acetone/t-BuOH/H₂O (5:1:1 V/V). At the room temperature, N-methylmorpholine-N-oxide (7.51 g) and OsO₄ (0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concentrated under reduced pressure. The concentrated residue was purified by a silica gel column chromatography to produce the title compound (6.42 g, yield 80%).

¹H NMR (400 MHz, CDCl₃) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 17: Synthesis of 1-(2-chlorophenyl)-(S,S)-1,2-butanediol

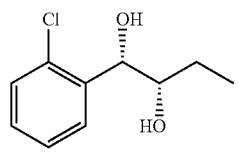

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 18: Synthesis of 1-(2-chlorophenyl)-(R,R)-1,2-butanediol

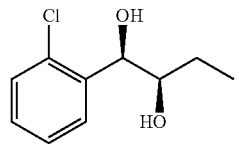

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 6095%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 19: Synthesis of the Mixture of 1-(2-chlorophenyl)-(S,S)-1,2-butanediol and 1-(2-chlorophenyl)-(R,R)-1,2-butanediol

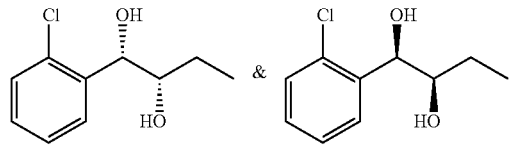

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 20: Synthesis of 1-(2-chlorophenyl)-3-methyl-(S,S)-1,2-butanediol

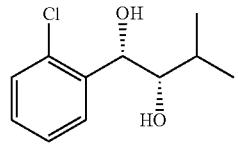

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

¹H NMR (400 MHz, CDCl₃) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 21: Synthesis of 1-(2-chlorophenyl)-3-methyl-(R,R)-1,2-butanediol

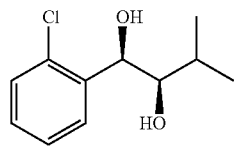

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).
¹H NMR (400 MHz, CDCl₃) δ1.07 (t, J=7.2 Hz, 6H), 1.82~1.90 (m, 1H), 1.93 (d, J=5.6 Hz, 1H), 2.79 (d, J=6 Hz, 1H), 3.53~3.57 (m, 1H), 5.23~5.25 (m, 1H), 7.23~7.54 (m, 4H)

Preparation Example 22: Synthesis of the Mixture of 1-(2-chlorophenyl)-3-methyl-(S,S)-1,2-butanediol and 1-(2-chlorophenyl)-3-methyl-(R,R)-1,2-butanediol

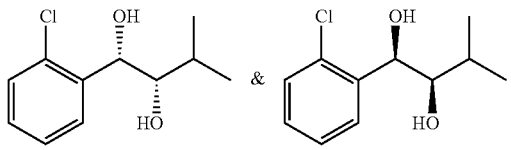

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).
¹H NMR (400 MHz, CDCl₃) δ1.07 (t, J=7.2 Hz, 6H), 1.83~1.90 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 23: Synthesis of 1-(2-chlorophenyl)-(S,S)-1,2-hexanediol

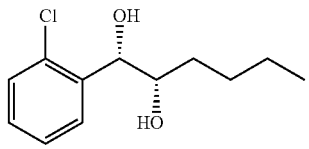

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).
¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.23~7.53 (m, 4H)

Preparation Example 24: Synthesis of 1-(2-chlorophenyl)-(R,R)-1,2-hexanediol

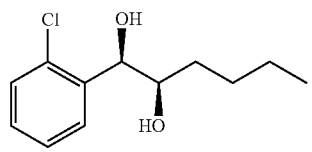

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).
¹H NMR (400 MHz, CDCl₃) δ0.91 (t, J=6.6 Hz, 3H), 1.35~1.65 (m, 6H), 2.08 (d, J=4.8 Hz, 1H), 2.70 (d, J=5.2 Hz, 1H), 3.80~3.83 (m, 1H), 5.05 (t, J=5.0 Hz, 1H), 7.24~7.56 (m, 4H)

Preparation Example 25: Synthesis of the Mixture of 1-(2-chlorophenyl)-(S,S)-1,2-hexanediol and 1-(2-chlorophenyl)-(R,R)-1,2-hexanediol

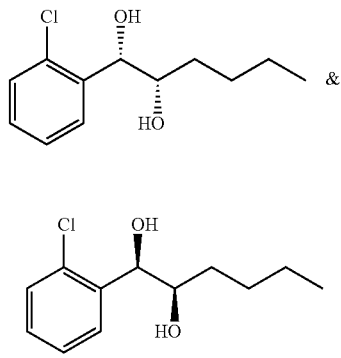

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).
¹H NMR (400 MHz, CDCl₃) δ0.90 (t, J=7.2 Hz, 3H), 1.26~4.55 (m, 6H), 2.08 (d, J=4.4 Hz, 1H), 2.71 (d, J=5.6 Hz, 1H), 3.78~3.84 (m, 1H), 5.04 (t, J=3.2 Hz, 7.24~7.55 (m, 4H)

Preparation Example 26: Synthesis of 1-(2,4-dichlorophenyl)-(S,S)-1,2-propanediol

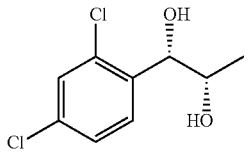

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 27: Synthesis of 1-(2,4-dichlorophenyl)-(R,R)-1,2-propanediol

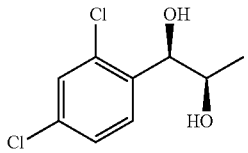

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 28: Synthesis of the Mixture of 1-(2,4-dichlorophenyl)-(S,S)-1,2-propanediol and 1-(2,4-dichlorophenyl)-(R,R)-1,2-propanediol

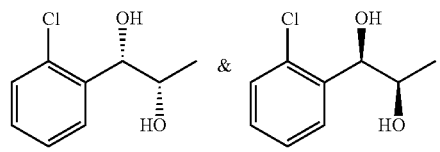

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 29: Synthesis of 1-(2,4-dichlorophenyl)-(S,S)-1,2-butanediol

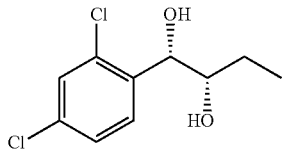

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR (400 MHz, CDCl$_3$) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 30: Synthesis of 1-(2,4-dichlorophenyl)-(R,R)-1,2-butanediol

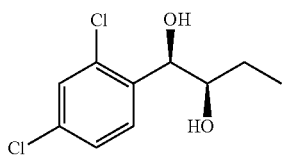

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR (400 MHz, CDCl$_3$) δ1.02 (t, J=7.4 Hz, 3H), 1.54~4.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 31: Synthesis of the Mixture of 1-(2,4-dichlorophenyl)-(S,S)-1,2-butanediol and 1-(2,4-dichlorophenyl)-(R,R)-1,2-butanediol

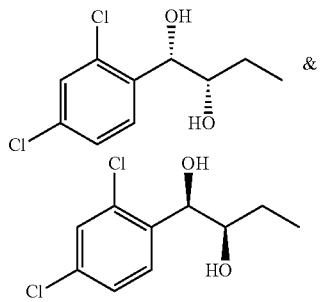

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

$^1$H NMR (400 MHz, CDCl$_3$) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 77.31~7.49 (m, 3H)

Preparation Example 32: Synthesis of 1-(2,4-dichlorophenyl)-3-methyl-(S,S)-1,2-butanediol

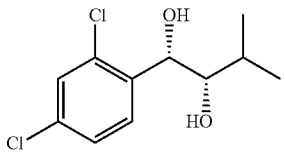

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

$^1$H NMR (400 MHz, CDCl$_3$) δ1.00 (d, J=6.8 Hz, 6H), 1.60~4.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 33: Synthesis of 1-(2,4-dichlorophenyl)-3-methyl-(R,R)-1,2-butanediol

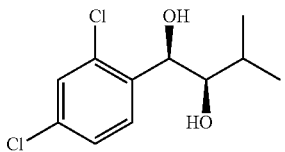

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 34: Synthesis of the Mixture of 1-(2,4-dichlorophenyl)-3-methyl-(S,S)-1,2-butanediol and 1-(2,4-dichlorophenyl)-3-methyl-(R,R)-1,2-butanediol

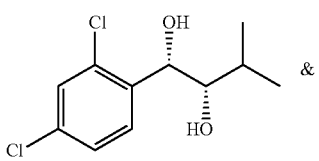

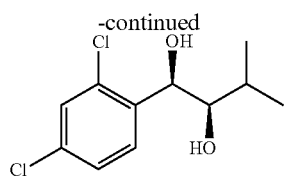

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 35: Synthesis of 1-(2,4-dichlorophenyl)-(S,S)-1,2-hexanediol

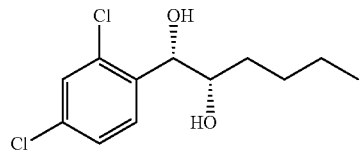 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.1 g, yield 60~90%).

$^1$H NMR (400 MHz, CDCl$_3$) δ0.89~0.93 (m, 3H), 1.30~1.39 (m, 2H), 1.49~4.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 36: Synthesis of 1-(2,4-dichlorophenyl)-(R,R)-1,2-hexanediol

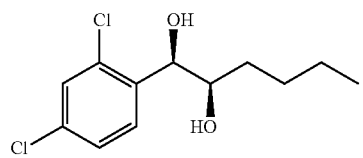 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.2 g, yield 60~95%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 37: Synthesis of the Mixture of 1-(2,4-dichlorophenyl)-(S,S)-1,2-hexanediol and 1-(2,4-dichlorophenyl)-(R,R)-1,2-hexanediol

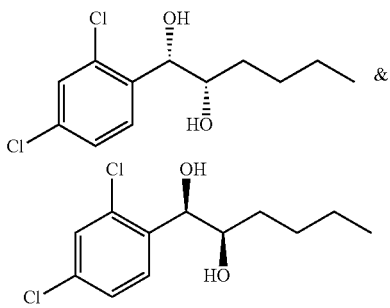

The substantially same method as described in Preparation Example 16 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (0.67 g, yield 60~95%).
$^1$H NMR (400 MHz, CDCl$_3$) δ0.89~0.93 (m, 3H), 1.30~1.39 (m, 2H), 1.49~4.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 38: Synthesis of 1-(2,6-dichlorophenyl)-(S,S)-1,2-propanediol

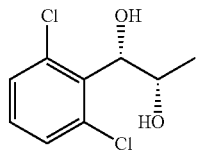

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 39: Synthesis of 1-(2,6-dichlorophenyl)-(R,R)-1,2-propanediol

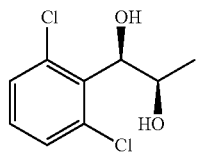

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 40: Synthesis of the Mixture of 1-(2,6-dichlorophenyl)-(S,S)-1,2-propanediol and 1-(2,6-dichlorophenyl)-(R,R)-1,2-propanediol

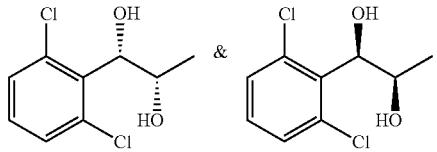

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 41: Synthesis of 1-(2,6-dichlorophenyl)-(S,S)-1,2-butanediol

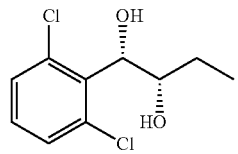

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).
$^1$H NMR (400 MHz, CDCl$_3$) δ0.97 (t, J=7.6 Hz, 3H), 1.26~4.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 42: Synthesis of 1-(2,6-dichlorophenyl)-(R,R)-1,2-butanediol

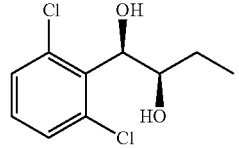

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

¹H NMR (400 MHz, CDCl₃) δ0.97 (t, J=7.6 Hz, 3H), 1.26~4.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 43: Synthesis of the Mixture of 1-(2,6-dichlorophenyl)-(S,S)-1,2-butanediol and 1-(2,6-dichlorophenyl)-(R,R)-1,2-butanediol

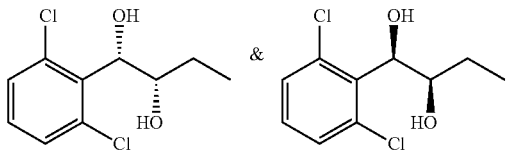

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 44: Synthesis of 1-(2,6-dichlorophenyl)-3-methyl-(S,S)-1,2-butanediol

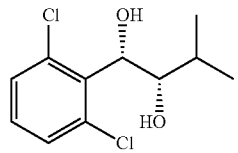

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 45: Synthesis of 1-(2,6-dichlorophenyl)-3-methyl-(R,R)-1,2-butanediol

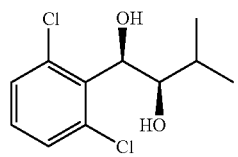

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

¹H NMR (400 MHz, CDCl₃) δ1.00 (d, J=6.8 Hz, 6H), 1.60~4.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 46: Synthesis of the Mixture of 1-(2,6-dichlorophenyl)-3-methyl-(S,S)-1,2-butanediol and 1-(2,6-dichlorophenyl)-3-methyl-(R,R)-1,2-butanediol

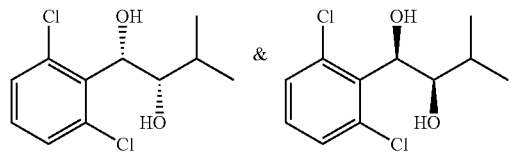

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 47: Synthesis of 1-(2,6-dichlorophenyl)-(S,S)-1,2-hexanediol

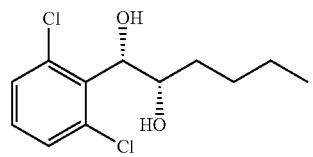 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

¹H NMR (400 MHz, CDCl₃) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 48: Synthesis of 1-(2,6-dichlorophenyl)-(R,R)-1,2-hexanediol

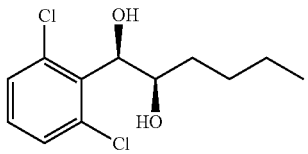 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR (400 MHz, CDCl$_3$) δ0.85 (t, J=6.8 Hz, 3H), 1.20~1.31 (m, 4H), 1.45~4.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 49: Synthesis of the Mixture of 1-(2,6-dichlorophenyl)-(S,S)-1,2-hexanediol and 1-(2,6-dichlorophenyl)-(R,R)-1,2-hexanediol

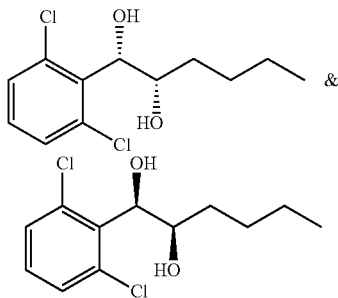

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR (400 MHz, CDCl$_3$) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 50: Synthesis of methyl 2-(2-chlorophenyl)-(R)-2-hydroxyacetate

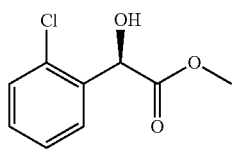

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (15.64 g, yield 95%).

$^1$H NMR (400 MHz, CDCl$_3$) δ 3.59 (d, J=5.2, 1H), 3.79 (t, J=6.0, 3H), 5.59 (d, J=5.2, 1H), 7.28~7.43 (m, 4H)

Preparation Example 51: Synthesis of 2-(2-chlorophenyl)-(R)-2-hydroxy-N-methoxy-N-methylacetamide

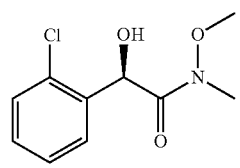

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concentrated under reduced pressure. The concentrated residue was purified by a silica gel column chromatography to produce the title compound (14.68 g, yield 82%).

$^1$H NMR (400 MHz, CDCl$_3$) δ3.23 (s, 3H), 3.28 (s, 3H), 4.33 (d, J=6.0 Hz, 1H), 5.81 (d, J=5.6 Hz, 1H), 7.23~7.42 (m, 4H)

Preparation Example 52: Synthesis of 2-(2-chlorophenyl)-N-methoxy-(R)-2-(t-butyl dimethlysiloxy)-N-methylacetamide

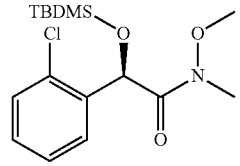

2-(2-chlorophenyl)-(R)-2-hydroxy-N-methoxy-N-methylacetamide (0.81 g, 3.52 mmol) obtained in Preparation Example 51 was dissolved in dichloromethane (DCM), and cooled to 0° C. Imedazole (0.36 g, 5.28 mmol) was slowly added, and stirred. TBDMS-Cl (t-butyldimethylsily chloride, 0.79 g, 5.28 mmol) was slowly added. When the reaction was completed, the reaction mixture was quenched with H₂O. The organic layer was separated and collected. The aqueous layer was extracted with CH₂Cl₂ (300 mL), dried over MgSO₄. Concentration under vacuum provided a title compound (0.97 g, 80~95%).

$^1$H NMR (400 MHz, CDCl₃) δ−0.03 (s, 3H), 0.14 (s, 3H), 0.94 (s, 9H), 2.97 (s, 3H), 3.02 (s, 3H), 5.83 (s, 1H), 7.25~7.60 (m, 4H)

Preparation Example 53: Synthesis of 1-(2-chlorophenyl)-(R)-1-(t-butyldimethyl-siloxy) propane-2-on

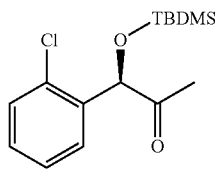

2-(2-chlorophenyl)-N-methoxy-(R)-2-(t-butyldimethylsiloxy)-N-methylacetamide (0.9 g) obtained in Preparation Example 52 was dissolved in tetrahydrofuran (THF), and cooled to 0° C. 3.0M methyl magnesium bromide (MeMgBr, 2.18 ml) solution in ether was added thereto in drop-wise manner for 30 minutes, and the obtained product was stirred at 0° C. When the reaction was completed, diethylether was added thereto. The obtained product was washed with 10% (w/v) potassium hydrogen sulfate (KHSO₄, 100 ml) and then, washed again with brine. The obtained organic layer was dehydrated with anhydrous magnesium sulfate (MgSO₄), filtrated, and concentrated under reduced pressure. The concentrated residue was purified by a silica gel column chromatography to produce the title compound (0.69 g, yield 85~95%).

$^1$H NMR (400 MHz, CDCl₃) δ−0.3 (s, 3H), 0.14 (s, 3H), 0.94 (s, 9H), 2.18 (s, 3H), 5.50 (s, 7.27~7.56 (m, 4H)

Preparation Example 54: Synthesis of 1-(2-chlorophenyl)-(R)-1-(t-butyldimethyl-siloxy)-(S)-2-propanol

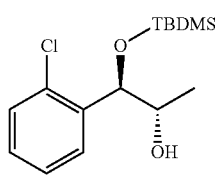

1-(2-chlorophenyl)-(R)-1-(t-butyldimethyl-siloxy)propane-2-on (0.14 g) obtained in Preparation Example 53 was dissolved in ether, and cooled to −78° C. Zinc borohydride (Zn(BH₄)₂) was slowly added thereto and the obtained product was stirred. When the reaction was completed, the obtained product was washed by H₂O. The obtained organic layer was washed with H₂O, dehydrated with anhydrous magnesium sulfate (MgSO₄), filtrated, and concentrated under reduced pressure. The concentrated residue was purified by a silica gel column chromatography to produce the title compound (0.04 g, yield 25~33%, cis:trans=2:1).

$^1$H NMR (400 MHz, CDCl₃) δ−0.11 (s, 3H), 0.11 (s, 3H), 0.93 (S, 9H), 1.07 (d, J=6.4 3H), 2.05 (d, J=6.4 1H), 4.01~4.05 (m, 1H), 5.18 (d, J=4.0, 1H), 7.20~7.56 (m, 4H)

Preparation Example 55: Synthesis of 1-(2-chlorophenyl)-(R,S)-1,2-propanediol

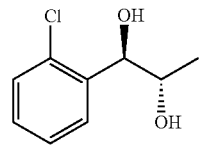

1-(2-chlorophenyl)-(R)-1-(t-butyldimethyl-siloxy)-(S)-2-propanol (10.38 g) obtained in Preparation Example 54 was dissolved in methanol (CH₃OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concentrated under reduced pressure. The concentrated residue was purified by a silica gel column chromatography to produce the title compound (7.05 g, yield 60~90%).

$^1$H NMR (400 MHz, CDCl₃) δ1.07 (d, J=6.8, 3H), 2.01 (d, J=5.6, 1H), 2.61 (s, 1H), 4.21~4.27 (m, 1H), 5.24 (d, J=3.6, 1H), 7.22~7.64 (m, 4H)

Preparation Example 56: Synthesis of 1-(2-chlorophenyl)-(S,R)-1,2-propanediol

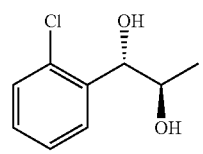

The substantially same method as described in Preparation Example 50~55 was conducted, except that (S)-2-chloromandelic acid was used instead of (R)-2-chloromandelic acid, to obtain the title compound (5.04 g, yield 84%).

$^1$H NMR (400 MHz, CDCl₃) δ1.07 (d, J=6.8, 3H), 2.00 (d, J=5.6, 1H), 2.54 (d, J=3.6, 1H), 4.22~4.26 (m, 1H), 5.25 (t, J=3.2, 1H), 7.22~7.65 (m, 4H)

Preparation Example 57: Synthesis of 1-(2,3-dichlorophenyl)-(S,S)-1,2-propanediol

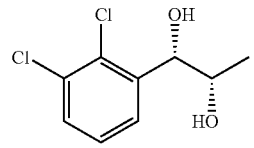

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 58: Synthesis of 1-(2,3-dichlorophenyl)-(R,R)-1,2-propanediol

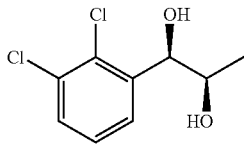

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 59: Synthesis of the Mixture of 1-(2,3-dichlorophenyl)-(S,S)-1,2-propanediol and 1-(2,3-dichlorophenyl)-(R,R)-1,2-propanediol

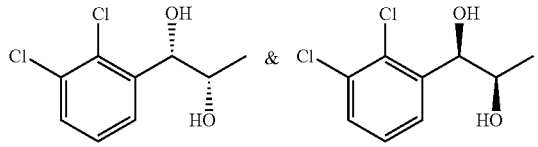

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 60: Synthesis of 1-(2-fluorophenyl)-trans-1-propene

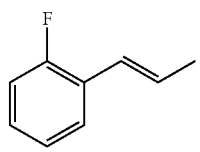

The substantially same method as described in Preparation Example 1 was conducted, except that 2-fluorobenzenaldehyde was used instead of 2-chlorobenzenealdehyde, to obtain the title compound (6.67 g, yield 61%).

¹H NMR (400 MHz, CDCl₃) δ1.94 (d, J=6.8 Hz, 3H), 6.30~6.38 (m, 1H), 6.57 (d, J=16 Hz, 1H), 7.00~7.41 (m, 4H)

Preparation Example 61: Synthesis of 1-(2-fluorophenyl)-(S,S)-1,2-propanediol

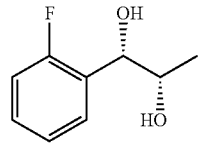

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

¹H NMR (400 MHz, CDCl₃) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 62: Synthesis of 1-(2-fluorophenyl)-(R,R)-1,2-propanediol

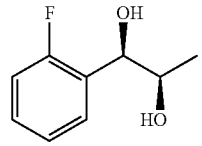

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

¹H NMR (400 MHz, CDCl₃) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 63: Synthesis of 2-iodobenzenealdehyde

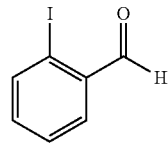

In a flask, 2-iodobenzyl alcohol (4 g, 17.09 mmol) was dissolved in dichloromethane (MC, 85 ml), and then, manganese oxide (MnO₂, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

$^1$H NMR (400 MHz, CDCl$_3$) δ7.30~7.99 (m, 4H), 10.10 (s, 1H)

Preparation Example 64: Synthesis of 1-(2-iodophenyl)-trans-1-propene

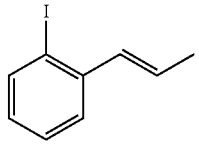

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR (400 MHz, CDCl$_3$) δ1.95 (dd, J=6.8 Hz, 1.6 Hz, 3H), 6.09~6.18 (m, 1H), 6.60 (dd, J=15.66 Hz, 1.8 Hz, 1H), 6.89~7.84 (m, 4H)

Preparation Example 65: Synthesis of 1-(2-iodophenyl)-trans-1-butene

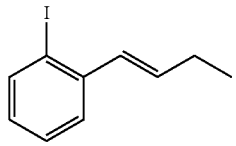

The substantially same method as described in Preparation Example 64 was conducted, except that 3-heptanone was used instead of 3-pentanone, to obtain the title compound (8.5 g, yield 75%).

$^1$H NMR (400 MHz, CDCl$_3$) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.89~7.85 (m, 4H)

Preparation Example 66: Synthesis of 1-(2-iodophenyl)-(S,S)-1,2-propanediol

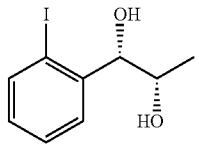

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR (400 MHz, CDCl$_3$) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01~7.87 (m, 4H)

Preparation Example 67: Synthesis of 1-(2-iodorophenyl)-(R,R)-1,2-propanediol

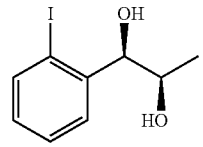

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR (400 MHz, CDCl$_3$) δ1.26 (d, J=6.4 Hz, 3H), 2.35 (br s, 1H), 2.85 (br d, J=4.0 Hz, 1H), 3.98 (t, J=6.2 Hz, 1H), 4.80 (dd, J=5.0, 4.4 Hz, 1H), 7.00~7.87 (m, 4H)

Preparation Example 68: Synthesis of 1-(2-iodophenyl)-(S,S)-1,2-butanediol

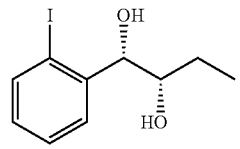

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR (400 MHz, CDCl$_3$) δ1.04 (t, J=7.6 Hz, 3H), 1.60~4.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 69: Preparation of 1-(2-chlorophenyl)-(S,S)-1,2-(Bis-trimethylsilanyloxy) propane

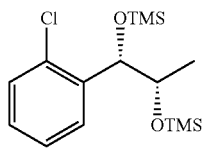

To a stirred solution of 1-(2-chlorophenyl)-(S,S)-1,2-propanediol (Preparation example 14, 67 g, 0.35 mol) in CH$_2$Cl$_2$ (670 ml) was added Et$_3$N (200 mL, 1.43 mol) and TMSCl (113.9 mL, 0.89 mol) at 0° C. under N$_2$. The reaction mixture was allowed to stir at 0° C. for 3 hr. The reaction mixture was quenched with H$_2$O (650 mL) at 0° C. The organic layer was separated and collected. The aqueous layer was extracted with CH$_2$Cl$_2$ (300 mL), dried over MgSO$_4$. Concentration under vacuum provided a crude product (104.18 g, 117.44%).

$^1$H NMR (400 MHz, CDCl$_3$) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.207~7.165 (m, 1H), 7.321~7.245 (m, 2H), 7.566~7.543 (m, 1H)

Preparation Example 70: Preparation of 1-(2-chlorophenyl)-(R,R)-1,2-(Bis-trimethylsilanyloxy) propane

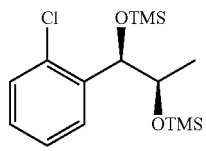

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).
$^1$H NMR (400 MHz, CDCl$_3$) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 71: Preparation of 1-(2-chlorophenyl)-1,2-(Bis-trimethylsilanyloxy) propane

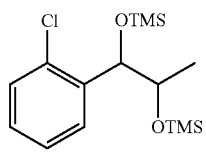

The substantially same method as described in Preparation Example 69 was conducted, except that 1-(2-chlorophenyl)propane-1,2-diol (Preparation example 16) was used instead of 1-(2-chlorophenyl)-(S,S)-1,2-propanediol (Preparation example 14) to obtain the title compound (5.2 g, yield 90~120%).
$^1$H NMR (400 MHz, CDCl$_3$) δ−0.053 (s, 9H), 0.044 (s, 9H), 1.15 (d, J=5.6 Hz, 3H), 3.977~3.918 (m, 1H), 4.973 (d, 1H), 7.21~7.54 (m, 4H)

Preparation Example 72: Preparation of 1-(2-chlorophenyl)-(S,R)-1,2-(Bis-trimethylsilanyloxy) propane

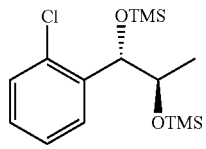

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).
$^1$H NMR (400 MHz, CDCl$_3$) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 73: Preparation of 1-(2-chlorophenyl)-(R,S)-1,2-(Bis-trimethylsilanyloxy) propane

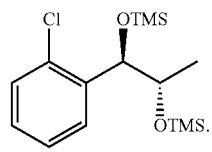

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).
$^1$H NMR (400 MHz, CDCl$_3$) δ−0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 74: Preparation of 1-(2-chlorophenyl)-(S,S)-1,2-(Bis-trimethylsilanyloxy) butane

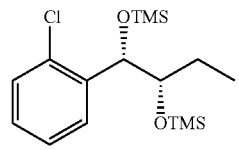

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).
$^1$H NMR (400 MHz, CDCl$_3$) δ−0.053 (s, 9H), 0.044 (s, 9H), 1.01 (t, J=7.4 Hz, 3H), 1.52~4.65 (m, 2H), 3.69~3.75 (m, 1H), 5.05 (t, J=5.0 Hz, 1H), 7.23~7.54 (m, 4H)

Preparation Example 75: Preparation of 1-(2-chlorophenyl)-(R,R)-1,2-(Bis-trimethylsilanyloxy) butane

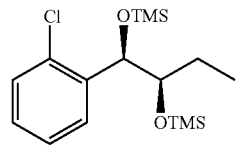

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).

$^1$H NMR (400 MHz, CDCl$_3$) δ−0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 76: Preparation of 1-(2-chlorophenyl)-1,2-(Bis-trimethylsilanyloxy) butane

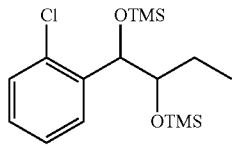

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).

$^1$H NMR (400 MHz, CDCl$_3$) δ−0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 77: Preparation of 1-(2-chlorophenyl)-3-methyl-(S,S)-1,2-(Bis-trimethylsilanyloxy)-butane

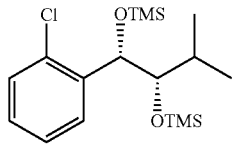

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title compound (2.7 g, yield 90~120%).

$^1$H NMR (400 MHz, CDCl$_3$) δ−0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 78: Preparation of 1-(2-chlorophenyl)-3-methyl-(R,R)-1,2-(Bis-trimethylsilanyloxy)-butane

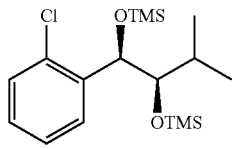

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).

$^1$H NMR (400 MHz, CDCl$_3$) δ−0.053 (s, 9H), 0.044 (s, 9H), 1.07 (t, J=7.2 Hz, 6H), 1.83~4.89 (m, 1H), 3.53~3.56 (m, 1H), 5.22~5.25 (m, 1H), 7.23~7.55 (m, 4H)

Preparation Example 79: Preparation of 1-(2-chlorophenyl)-3-methyl-1,2-(Bis-trimethylsilanyloxy)-butane

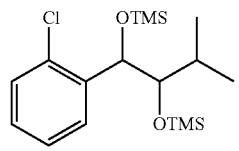

The substantially same method as described in Preparation Example 69 was conducted, except that 1-(2-chlorophenyl)-3-methyl-1,2-butanediol (Preparation example 22) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ−0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 80: Preparation of 1-(2-chlorophenyl)-(S,S)-1,2-(Bis-trimethylsilanyloxy)-hexane

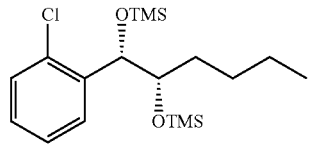

The substantially same method as described in Preparation Example 69 was conducted, except that 1-(2-chlorophenyl)-(S,S)-1,2-hexanediol (Preparation example 23) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 81: Preparation of 1-(2-chlorophenyl)-(S,S)-1,2-(Bis-trimethylsilanyloxy)-hexane

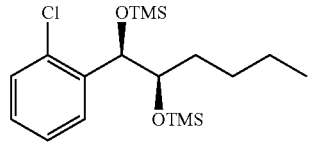

The substantially same method as described in Preparation Example 69 was conducted, except that 1-(2-chlorophenyl)-(R,R)-1,2-hexanediol (Preparation example 24) was used instead of 1-(2-chlorophenyl)-(S,S)-1,2-propanediol (Preparation example 14) to obtain the title compound (3.3 g, yield 90~120%).

¹H NMR (400 MHz, CDCl₃) δ−0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 82: Preparation of 1-(2-chlorophenyl)-(S,S)-1,2-(Bis-trimethylsilanyloxy)-hexane

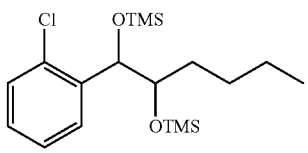

The substantially same method as described in Preparation Example 69 was conducted, except that 1-(2-chlorophenyl)-1,2-hexanediol (Preparation example 25) was used instead of 1-(2-chlorophenyl)-(S,S)-1,2-propanediol (Preparation example 14) to obtain the title compound (3.2 g, yield 90~120%).

¹H NMR (400 MHz, CDCl₃) δ−0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 83: Preparation of 1-(2,4-dichlorophenyl)-(S,S)-1,2-(Bis-trimethylsilanyloxy)-propane

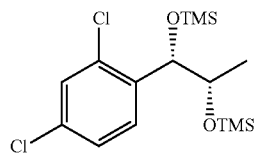

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90~120%).

¹H NMR (400 MHz, CDCl₃) δ−0.053 (s, 9H), 0.044 (s, 9H), 1.22 (d, J=6.4 Hz, 3H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 84: Preparation of 1-(2,6-dichlorophenyl)-(S,S)-1,2-(Bis-trimethylsilanyloxy)-propane

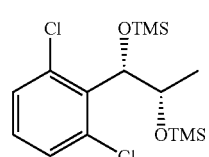

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).

¹H NMR (400 MHz, CDCl₃) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.13~7.36 (m, 3H)

Preparation Example 85: Preparation of 1-(2,3-dichlorophenyl)-(S,S)-1,2-(Bis-trimethylsilanyloxy)-propane

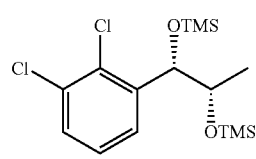

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).

¹H NMR (400 MHz, CDCl₃) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 86: Preparation of 1-(2,4-dichlorophenyl)-(S,S)-1,2-(Bis-trimethylsilanyloxy)-butane

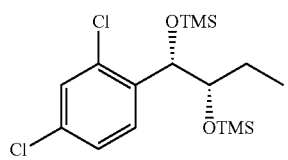

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).

¹H NMR (400 MHz, CDCl₃) δ−0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 87: Preparation of 1-(2,6-dichlorophenyl)-(S,S)-1,2-(Bis-trimethylsilanyloxy)-butane

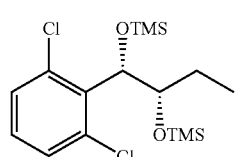

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ −0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 88: Preparation of 1-(2,4-dichlorophenyl)-3-methyl-(S,S)-1,2-(Bis-trimethylsilanyloxy)-butane

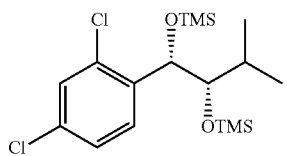

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).

$^1$H NMR (400 MHz, CDCl$_3$) δ −0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 89: Preparation of 1-(2,6-dichlorophenyl)-3-methyl-(S,S)-1,2-(Bis-trimethylsilanyloxy)-butane

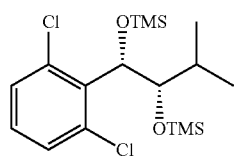

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ −0.053 (s, 9H), 0.044 (s, 9H), 1.00 (d, 6H), 1.60~1.65 (m, 1H), 4.13~4.18 (m, 1H), 5.36 (t, J=7.61 Hz, 1H), 7.17~7.35 (m, 3H)

Preparation Example 90: Preparation of 1-(2,4-dichlorophenyl)-(S,S)-1,2-(Bis-trimethylsilanyloxy)-hexane

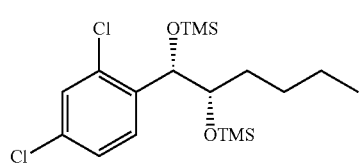

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

$^1$H NMR (400 MHz, CDCl$_3$) δ −0.053 (s, 9H), 0.044 (s, 9H), 0.89~0.93 (m, 3H), 1.30~1.39 (m, 2H), 1.49~1.52 (m, 2H), 1.56~1.6 (m, 2H), 3.72~3.77 (m, 1H), 4.98 (t, 1H), 7.28~7.50 (m, 3H)

Preparation Example 91: Preparation of 1-(2,6-dichlorophenyl)-(S,S)-1,2-(Bis-trimethylsilanyloxy)-hexane

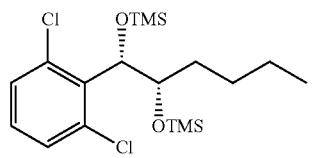

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ −0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 92: Preparation of 1-(2,4-dichlorophenyl)-(R,R)-1,2-(Bis-trimethylsilanyloxy)-propane

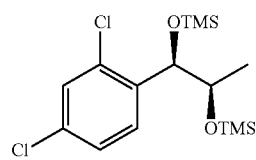

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

$^1$H NMR (400 MHz, CDCl$_3$) δ −0.053 (s, 9H), 0.044 (s, 9H), 1.22 (d, J=6.4 Hz, 3H), 3.90~3.95 (m, 1H), 4.94 (t, J=5.0 Hz, 1H), 7.31~7.49 (m, 3H)

Preparation Example 93: Preparation of 1-(2,6-dichlorophenyl)-(R,R)-1,2-(Bis-trimethylsilanyloxy)-propane

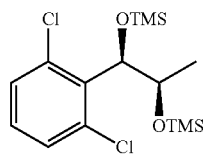

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.36 (m, 3H)

Preparation Example 94: Preparation of 1-(2,3-dichlorophenyl)-(R,R)-1,2-(Bis-trimethylsilanyloxy)-propane

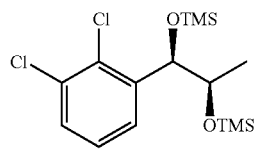

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 95: Preparation of 1-(2,4-dichlorophenyl)-(R,R)-1,2-(Bis-trimethylsilanyloxy)-butane

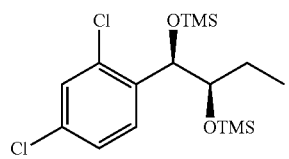

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

$^1$H NMR (400 MHz, CDCl$_3$) δ−0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 96: Preparation of 1-(2,6-dichlorophenyl)-(R,R)-1,2-(Bis-trimethylsilanyloxy)-butane

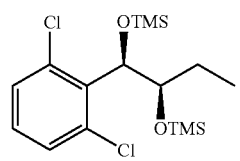

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ−0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 97: Preparation of 1-(2,4-dichlorophenyl)-3-methyl-(R,R)-1,2-(Bis-trimethylsilanyloxy)-butane

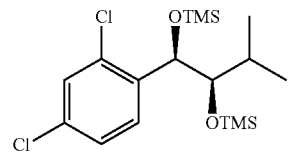

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).

$^1$H NMR (400 MHz, CDCl$_3$) δ−0.053 (s, 9H), 0.044 (s, 9H), 1.00 (d, J=6.8 Hz, 6H), 1.60~4.65 (m, 1H), 4.13~4.18 (m, 1H), 5.36 (t, J=7.6 Hz, 1H), 7.30~7.53 (m, 3H)

Preparation Example 98: Preparation of 1-(2,6-dichlorophenyl)-3-methyl-(R,R)-1,2-(Bis-trimethylsilanyloxy)-butane

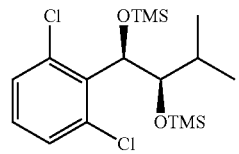

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-

1,2-propanediol (Preparation example 14) to obtain the title compound (3.4 g, yield 90~120%).

$^1$H NMR (400 MHz, CDCl$_3$) δ−0.053 (s, 9H), 0.044 (s, 9H), 1.00 (d, 6H), 1.60~1.65 (m, 1H), 4.13~4.18 (m, 1H), 5.36 (t, J=7.6 Hz, 1H), 7.17~7.35 (m, 3H)

Preparation Example 99: Preparation of 1-(2,4-dichlorophenyl)-(R,R)-1,2-(Bis-trimethylsilanyloxy)-hexane

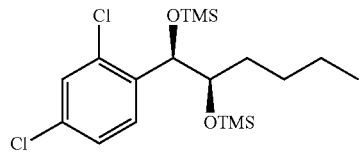

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).

$^1$H NMR (400 MHz, CDCl$_3$) δ−0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, 1H), 7.28~7.50 (m, 3H)

Preparation Example 100: Preparation of 1-(2,6-dichlorophenyl)-(R,R)-1,2-(Bis-trimethylsilanyloxy)-hexane

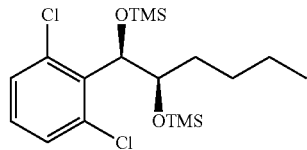

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ−0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 101: Preparation of 1-(2,4-dichlorophenyl)-1,2-(Bis-trimethylsilanyloxy)-propane

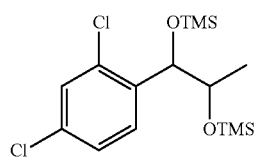

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ−0.053 (s, 9H), 0.044 (s, 9H), 1.22 (d, J=6.4 Hz, 3H), 3.90~3.95 (m, 1H), 4.94 (t, J=5.0 Hz, 1H), 7.31~7.49 (m, 3H)

Preparation Example 102: Preparation of 1-(2,6-dichlorophenyl)-1,2-(Bis-trimethylsilanyloxy)-propane

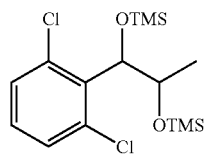

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.36 (m, 3H)

Preparation Example 103: Preparation of 1-(2,3-dichlorophenyl)-1,2-(Bis-trimethylsilanyloxy)-propane

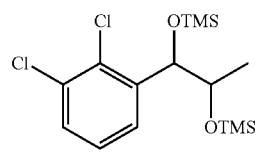

The substantially same method, described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90~120%).

$^1$H NMR (400 MHz, CDCl$_3$) δ−0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 104: Preparation of 1-(2,4-dichlorophenyl)-1,2-(Bis-trimethylsilanyloxy)-butane

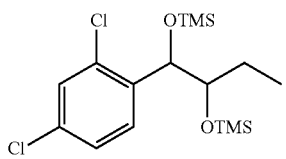

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).

$^1$H NMR (400 MHz, CDCl$_3$) δ–0.053 (s, 9H), 0.044 (s, 9H), 1.02 (t, J=7.4 Hz, 3H), 1.54~4.61 (m, 2H), 3.65~3.68 (m, 1H), 5.01 (t, J=5.0 Hz, 1H), 7.31~7.49 (m, 3H)

Preparation Example 105: Preparation of 1-(2,6-dichlorophenyl)-1,2-(Bis-trimethylsilanyloxy)-butane

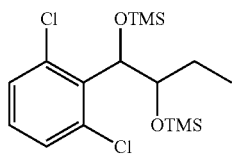

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ–0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 106: Preparation of 1-(2,4-dichlorophenyl)-3-methyl-1,2-(Bis-trimethylsilanyloxy)-butane

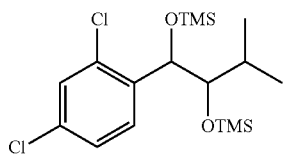

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~120%).

$^1$H NMR (400 MHz, CDCl$_3$) δ–0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 107: Preparation of 1-(2,6-dichlorophenyl)-3-methyl-1,2-(Bis-trimethylsilanyloxy)-butane

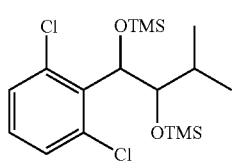

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ–0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 108: Preparation of 1-(2,4-dichlorophenyl)-1,2-(Bis-trimethylsilanyloxy)-hexane

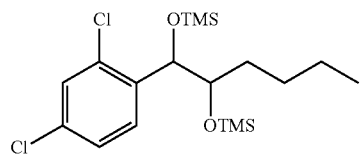

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).

$^1$H NMR (400 MHz, CDCl$_3$) δ–0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8 Hz, 1H), 7.28~7.50 (m, 3H)

Preparation Example 109: Preparation of 1-(2,6-dichlorophenyl)-1,2-(Bis-trimethylsilanyloxy)-hexane

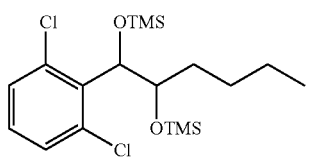

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).

$^1$H NMR (400 MHz, CDCl$_3$) δ–0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 110: Preparation of 1-(2-fluoroophenyl)-(S,S)-1,2-(Bis-trimethylsilanyloxy)-propane

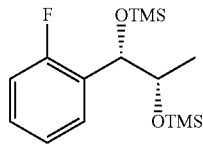

The substantially same method as described in Preparation Example 69 was conducted, except that 1-(2-fluoroophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ−0.053 (s, 9H), 0.044 (s, 9H), 1.15 (d, J=6.4 Hz, 3H), 3.90~3.98 (m, 1H), 4.78 (dd, J=4.4, 7.2 Hz, 1H), 7.04~7.50 (m, 4H)

Preparation Example 111: Preparation of 1-(2-fulorophenyl)-(R,R)-1,2-(Bis-trimethylsilanyloxy)-propane

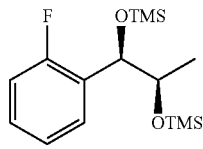

The substantially same method as described in Preparation Example 69 was conducted, except that 1-(2-fluoroophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

$^1$H NMR (400 MHz, CDCl$_3$) δ−0.053 (s, 9H), 0.044 (s, 9H), 1.15 (d, J=6.4 Hz, 3H), 3.90~3.98 (m, 1H), 4.78 (dd, J=4.4, 7.2 Hz, 1H), 7.04~7.50 (m, 4H)

Preparation Example 112: Preparation of 1-(2-iodophenyl)-(S,S)-1,2-(Bis-trimethylsilanyloxy)-propane

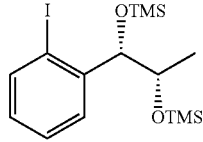

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ−0.053 (s, 9H), 0.044 (s, 9H), 1.27 (d, J=6.4 Hz, 3H), 3.99 (t, J=6.0 Hz, 1H), 4.81 (d, J=4.0 Hz, 1H), 7.01~7.87 (m, 4H)

Preparation Example 113: Preparation of 1-(2-iodophenyl)-(R,R)-1,2-(Bis-trimethylsilanyloxy)-propane

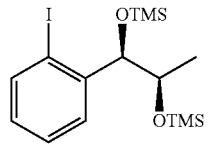

The substantially same method as described in Preparation Example 69 was conducted, except that 1-(2-iodophenyl)-(R,R)-1,2-propanediol (Preparation example 67) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ−0.053 (s, 9H), 0.044 (s, 9H), 1.26 (d, J=6.4 Hz, 3H), 3.98 (t, J=6.2 Hz, 1H), 4.88 (d, J=4.4 Hz, 1H), 7.00~7.87 (m, 4H)

Preparation Example 114: Preparation of 1-(2-iodophenyl)-(S,S)-1,2-(Bis-trimethylsilanyloxy)-butane

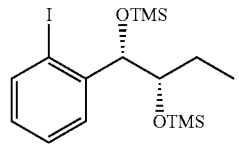

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ−0.053 (s, 9H), 0.044 (s, 9H), 1.04 (t, J=7.6 Hz, 3H), 1.60~1.71 (m, 2H), 3.71~3.76 (m, 1H), 4.87 (d, J=4.8 Hz, 1H), 7.01~7.87 (m, 4H)

Table 1: Example of Sulfamate Compound
 *: Sodium Salt

Example 1: Preparation of 1-(2-chlorophenyl)-(S)-1-hydroxypropyl-(S)-2-carbamate (1)

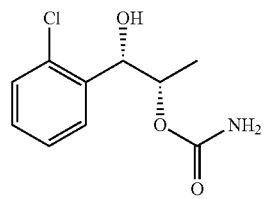

To a stirred solution of crude 1-(2-chlorophenyl)-(S,S)-1,2-(Bis-trimethylsilanyloxy) propane (preparation example 69, 104 g, 0.31 mol) in toluene (670 mL) was added by Chlorosulfonyl isocynate (62.5 mL, 0.71 mol) at 0° C. The reaction mixture was stirred for 2 hr. The reaction mixture was quenched with ice water and then was stirred by additional cold H$_2$O (500 mL) for 2 hr. After separation of organic layer, the aqueous was adjusted pH2~3 with sat.

NaHCO$_3$ (400 mL) and extracted with EtOAc (300 mL×3). The EtOAc layer was washed with sat. NaHCO$_3$ (500 mL) and H$_2$O (500 mL). The organic phase was treated with Charcol for 1.5 hr. The organic phase was filtered with Cellite, dried over MgSO$_4$. Filterion and concentration under vacuum provided the title compound of white solid (yield 85%(71.1 g), ee=99.9% MP=83~84, [α]D=+57.8 (c=0.25, MeOH))

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, 1H)

$^{13}$C NMR (100 MHz, CDCl$_3$) δ16.4, 73.1, 75.0, 127.0, 128.4, 129.1, 129.5, 132.7, 138.0, 156.6

Example 2: Preparation of 1-(2-chlorophenyl)-(R)-1-hydroxypropyl-(R)-2-carbamate (2)

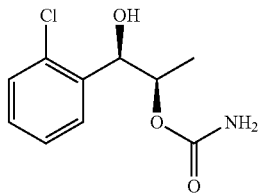

The substantially same method as described in Example 1 was conducted, except that 1-(2-chlorophenyl)-(R,R)-1,2-(Bis-trimethylsilanyloxy) propane (Preparation example 70) was used instead of 1-(2-chlorophenyl)-(S,S)-1,2-(Bis-trimethylsilanyloxy) propane (Preparation example 69) to obtain the title compound (5.7 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 3: Preparation of 1-(2-chlorophenyl)-1-hydroxypropyl-2-carbamate (3)

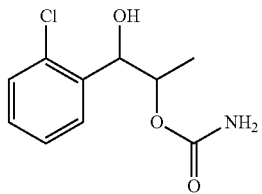

The substantially same method as described in Example 1 was conducted, except that 1-(2-chlorophenyl)-1,2-(Bis-trimethylsilanyloxy) propane (Preparation example 71) was used instead of 1-(2-chlorophenyl)-(S,S)-1,2-(Bis-trimethylsilanyloxy) propane (Preparation example 69) to obtain the title compound (3.8 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 4: Preparation of 1-(2-chlorophenyl)-(S)-1-hydroxypropyl-(R)-2-carbamate (4)

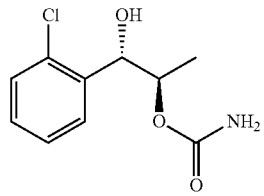

The substantially same method as described in Example 1 was conducted, except that 1-(2-chlorophenyl)-(S,R)-1,2-(Bis-trimethylsilanyloxy) propane (Preparation example 72) was used instead of 1-(2-chlorophenyl)-(S,S)-1,2-(Bis-trimethyl silanyloxy) propane (Preparation example 69) to obtain the title compound (2.4 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 5: Preparation of 1-(2-chlorophenyl)-(R)-1-hydroxypropyl-(S)-2-carbamate (5)

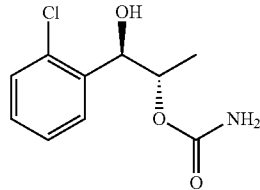

The substantially same method as described in Example 1 was conducted, except that 1-(2-chlorophenyl)-(R,S)-1,2-(Bis-trimethylsilanyloxy) propane (Preparation example 73) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR (400 MHz, CDCl$_3$) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 6: Preparation of 1-(2-chlorophenyl)-(S)-1-hydroxybutyl-(S)-2-carbamate (6)

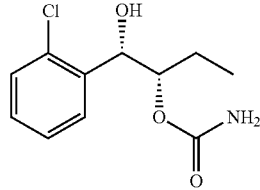 [SMILES: CC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR (400 MHz, CDCl$_3$) δ0.96 (t, J=7.4 Hz, 3H), 1.57~1.73 (m, 2H), 3.01 (d, J=5.6 Hz, 1H), 4.74 (br s, 2H), 4.95 (dt, J=7.2, 8.8 Hz, 1H), 5.23 (t, J=5.6 Hz, 1H), 7.22~7.54 (m, 4H)

Example 7: Synthesis of 1-(2-chlorophenyl)-(R)-1-hydroxybtyl-(R)-2-carbamate (7)

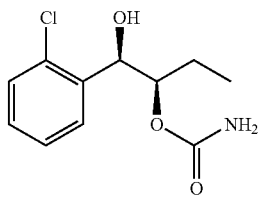 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy) propane (Preparation example 69) to obtain the title compound (2.5 g, yield 60~90%).
$^1$H NMR (400 MHz, CDCl$_3$) δ 0.94 (t, J=7.4 Hz, 3H), 1.53~1.73 (m, 2H), 2.92 (s, 1H), 4.78 (br s, 2H), 4.91~4.96 (m, 1H), 5.22 (d, J=5.5 Hz, 1H), 7.20~7.54 (m, 4H)

Example 8: Synthesis of 1-(2-chlorophenyl)-1-hydroxybutyl-2-carbamate (8)

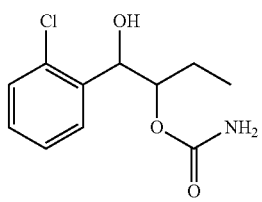 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy) propane (Preparation example 69) to obtain the title compound (1.9 g, yield 60~90%).
$^1$H NMR (400 MHz, CDCl$_3$) δ 0.97 (t, J=7 Hz, 3H), 1.58~1.74 (m, 2H), 2.94 (d, J=6 Hz, 1H), 4.69 (br s, 2H), 4.94~4.99 (m, 1H), 5.24 (t, J=6 Hz, 1H), 7.23~7.56 (m, 4H)

Example 9: Synthesis of 1-(2-chlorophenyl)-(S)-1-hydroxy-3-methyl-butyl-(S)-2-carbamate(9)

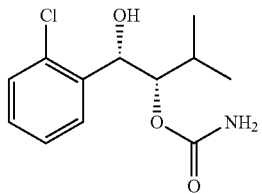

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy) propane (Preparation example 69) to obtain the title compound (1.7 g, yield 60~90%).
$^1$H NMR (400 MHz, CDCl$_3$) δ1.01 (d, J=6.4 Hz, 3H), 1.09 (d, J=6.8 Hz, 3H), 2.06 (m, 1H), 2.75 (d, J=6.8 Hz, 1H), 4.58 (br s, 2H), 4.85~4.88 (m, 1H), 5.34~5.37 (m, 1H), 7.22~7.33 (m, 2H), 7.35~7.37 (m, 1H), 7.51~7.53 (m, 1H)

Example 10: Synthesis of 1-(2-chlorophenyl)-(R)-1-hydroxy-3-methyl-butyl-(R)-2-carbamate (10)

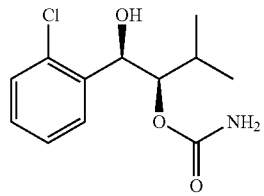 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy) propane (Preparation example 69) to obtain the title compound (1.6 g, yield 60~90%).
$^1$H NMR (400 MHz, CDCl$_3$) δ1.01 (d, J=6.8 Hz, 3H), 1.09 (d, J=6.8 Hz, 3H), 2.06 (m, 1H), 2.73 (d, J=6.8 Hz, 1H), 4.57 (br s, 2H), 4.85~4.88 (m, 1H), 5.34~5.37 (m, 1H), 7.24~7.30 (m, 2H), 7.35~7.37 (m, 1H), 7.51~7.53 (m, 1H)

Example 11: Synthesis of 1-(2-chlorophenyl)-1-hydroxy-3-methyl-butyl-2-carbamate (11)

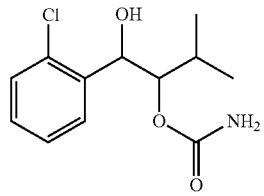 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy) propane (Preparation example 69) to obtain the title compound (1.7 g, yield 60~90%).
$^1$H NMR (400 MHz, CDCl$_3$) δ1.00 (d, J=6.4 Hz, 3H), 1.09 (d, J=6.4 Hz, 3H), 2.08 (m, 1H), 2.76 (d, J=6.0 Hz, 4.59 (br s, 2H), 4.87 (dd, J=7.2 Hz, 4.4 Hz, 1H), 5.36 (t, J=4.6, 1H), 7.23~7.54 (m, 4H)

Example 12: Synthesis of 1-(2-chlorophenyl)-(S)-1-hydroxyhexyl-(S)-2-carbamate (12)

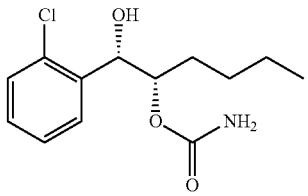 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy) propane (Preparation example 69) to obtain the title compound (2.3 g, yield 60~90%).

$^{1}$H NMR (400 MHz, CDCl$_3$) δ0.88 (t, J=7 Hz, 3H), 1.33~1.42 (m, 4H), 1.53~1.71 (m, 2H), 2.89 (d, J=5.6 Hz, 1H) 4.64 (br s, 2H), 5.04 (dt, J=5.0, 9.0 Hz, 1H), 5.20 (t, J=5.6 Hz, 1H), 7.23~7.55 (m, 4H)

Example 13: Synthesis of 1-(2-chlorophenyl)-(R)-1-hydroxyhexyl-(R)-2-carbamate (13)

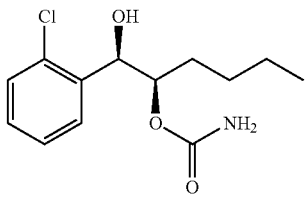 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy) propane (Preparation example 69) to obtain the title compound (2.2 g, yield 60~90%).

$^{1}$H NMR (400 MHz, CDCl$_3$) δ 0.89 (dd, J=5 Hz, 3H), 1.28~1.43 (m, 4H), 1.52~1.58 (m, 1H), 1.65~1.72 (m, 1H), 2.90 (d, J=6 Hz, 1H), 4.64 (br s, 2H), 5.01~5.06 (m, 1H), 5.22 (t, J=6 Hz, 1H), 7.22~7.56 (m, 4H)

Example 14: Synthesis of 1-(2-chlorophenyl)-1-hydroxyhexyl-2-carbamate (14)

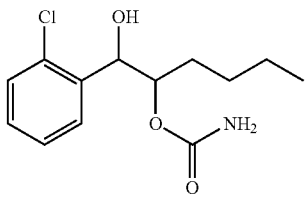 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy) propane (Preparation example 69) to obtain the title compound (2.1 g, yield 60~90%).

$^{1}$H NMR (400 MHz, CDCl$_3$) δ 0.88 (dd, J=5 Hz, 3H), 1.31~1.43 (m, 4H), 1.63~1.70 (m, 1H), 1.52~1.60 (m, 1H), 3.06 (d, J=6 Hz, 1H), 4.75 (br s, 2H), 5.00~5.05 (m, 1H), 5.21 (t, J=6 Hz, 1H), 7.22~7.55 (m, 4H)

Example 15: Synthesis of 1-(2-chlorophenyl)-(S)-1-hydroxypropyl-(S)-2-N-methylcarbamate (15)

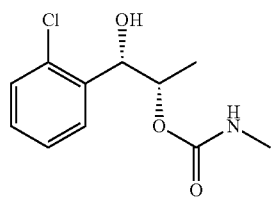 [SMILES: CNC(=O)O[C@@H](C)[C@@H](O)c1ccccc1Cl]

1-(2-chlorophenyl)-(S,S)-1,2-propanediol (2.4 g) obtained in Preparation Example 14, tetrahydrofuran (THF, 12 ml), and carbonyldiimidazole (CDI, 3.12 g) were put into a flask and stirred at the room temperature. After approximately 3 hours, methylamine solution (CH$_3$NH$_2$, 4 ml (33% in EtOH)) was added thereto. When the reaction was completed, the obtained product was washed with 1M HCl solution and ethylacetate (EA). The separated organic layer was dehydrated with anhydrous magnesium sulfate (MgSO$_4$), filtrated, and concentrated under reduced pressure. The concentrated residue was purified by a silica gel column chromatography, to obtain the title compound (1.6 g, yield 51%).

$^{1}$H NMR (400 MHz, CDCl$_3$) δ1.03~1.25 (m, 3H), 2.76 (s, 3H), 3.34 (s, 1H), 4.80 (br s 1H), 5.04 (t, J=12.5 Hz, 1H), 5.14 (s, 1H), 7.20~7.53 (m, 4H)

Example 16: Synthesis of 1-(2-chlorophenyl)-(S)-1-hydroxypropyl-(S)-2-N-propylcarbamate (16)

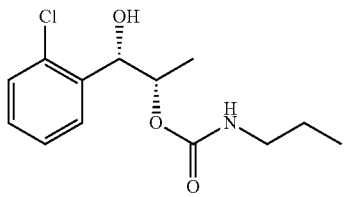 [SMILES: CCCNC(=O)O[C@@H](C)[C@@H](O)c1ccccc1Cl]

The substantially same method as described in Example 15 was conducted, except that propylamine was used instead of methylamine solution (CH$_3$NH$_2$ in EtOH), to obtain the title compound (0.79 g, yield 25%).

$^{1}$H NMR (400 MHz, CDCl$_3$) δ0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 7.22~7.53 (m, 4H)

Example 17: Synthesis of 1-(2-chlorophenyl)-(S)-1-hydroxypropyl-(R)-2-N-isopropylcarbamate (17)

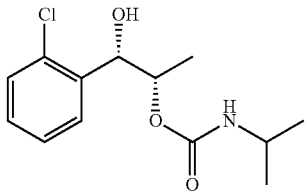 [SMILES: CC(C)NC(=O)O[C@@H](C)[C@@H](O)c1ccccc1Cl]

The substantially same method as described in Example 15 was conducted, except that isopropylamine was used instead of methylamine solution (CH$_3$NH$_2$ in EtOH), to obtain the title compound (1.5 g, yield 41%).

$^1$H NMR (400 MHz, CDCl$_3$) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.20~7.53 (m, 4H)

Example 18: Synthesis of 1-(2-chlorophenyl)-(S)-1-hydroxypropyl-(R)-2-N-cyclopropylcarbamate (18)

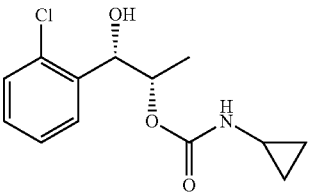 [SMILES: C[C@H](OC(=O)NC1CC1)[C@@H](O)c1ccccc1Cl]

The substantially same method as described in Example 15 was conducted, except that cyclopropylamine was used instead of methylamine solution (CH$_3$NH$_2$ in EtOH), to obtain the title compound (2.2 g, yield 43%).

$^1$H NMR (400 MHz, CDCl$_3$) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.23~7.54 (m, 4H)

Example 19: Synthesis of 1-(2-chlorophenyl)-(S)-1-hydroxypropyl-(R)-2-N-cyclohexyl carbamate (19)

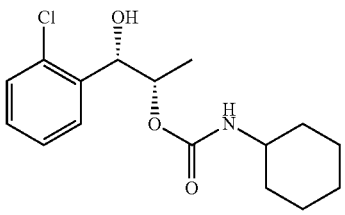 [SMILES: C[C@H](OC(=O)NC1CCCCC1)[C@@H](O)c1ccccc1Cl]

The substantially same method as described in Example 15 was conducted, except that cyclohexylamine was used instead of methylamine solution (CH$_3$NH$_2$ in EtOH), to obtain the title compound (1.1 g, yield 26%).

$^1$H NMR (400 MHz, CDCl$_3$) δ1.06~4.40 (m, 7H), 1.56~4.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.20~7.53 (m, 4H)

Example 20: Synthesis of 1-(2-chlorophenyl)-(S)-1-hydroxypropyl-(S)-2-N-benzyl carbamate (20)

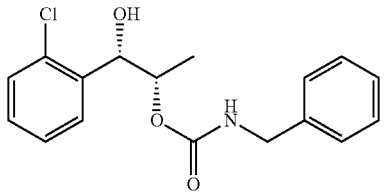 [SMILES: C[C@H](OC(=O)NCc1ccccc1)[C@@H](O)c1ccccc1Cl]

The substantially same method as described in Example 15 was conducted, except that benzylamine was used instead of methylamine solution (CH$_3$NH$_2$ in EtOH), to obtain the title compound (1.2 g, yield 18%).

$^1$H NMR (400 MHz, CDCl$_3$) δ 1.27 (d, J=10 Hz, 3H), 3.12 (d, J=5 Hz, 1H), 4.37 (d, J=6 Hz, 2H), 5.12~5.19 (m, 3H), 7.15~7.56 (m, 9H)

Example 21: Synthesis of 1-(2-chlorophenyl)-(S)-1-hydroxypropyl-(S)-2-N-bicyclo[2,2,1]heptanescarbamate (21)

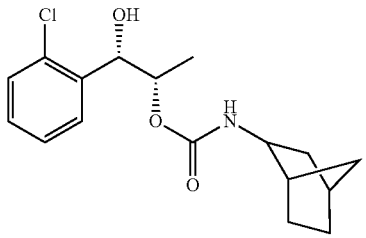 [SMILES: C[C@H](OC(=O)NC1CC2CCC1C2)[C@@H](O)c1ccccc1Cl]

The substantially same method as described in Example 15 was conducted, except that 2-aminonorbornane was used instead of methylamine solution (CH$_3$NH$_2$ in EtOH), to obtain the title compound (1.7 g, yield 32%).

$^1$H NMR (400 MHz, CDCl$_3$) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 22: Synthesis of 1-(2-chlorophenyl)-(R)-1-hydroxypropyl-(R)-2-N-methylcarbamate (22)

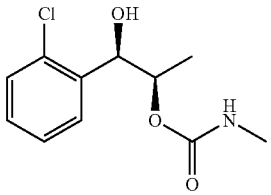 [SMILES: CNC(=O)O[C@H](C)[C@H](O)c1ccccc1Cl]

The substantially same method as described in Example 15 was conducted, except that 1-(2-chlorophenyl)-(R,R)-1, 2-propanediol (Preparation example 15) was used instead of 1-(2-chlorophenyl)-(S,S)-1,2-propanediol (Preparation example 14), to obtain the title compound (3.36 g, yield 60%).

$^1$H NMR (400 MHz, CDCl$_3$) δ 1.20 (d, J=6.8 Hz, 3H), 2.80 (d, J=4.8 Hz, 3H), 3.20 (d, J=4.4 Hz, 1H), 4.75 (br s, 1H), 5.03~5.09 (m, 1H), 5.14~5.17 (m, 1H), 7.22~7.55 (m, 4H)

Example 23: Synthesis of 1-(2-chlorophenyl)-(R)-1-hydroxypropyl-(R)-2-N-propylcarbamate (23)

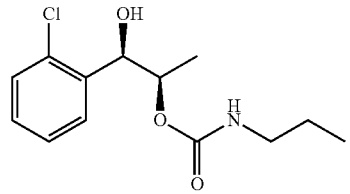 [SMILES: CCCNC(=O)O[C@H](C)[C@H](O)c1ccccc1Cl]

The substantially same method as described in Example 22 was conducted, except that propylamine was used instead of methylamine solution (CH$_3$NH$_2$ in EtOH), to obtain the title compound (3.1 g, yield 53%).

$^1$H NMR (400 MHz, CDCl$_3$) δ0.92 (t, J=7.6 Hz, 3H), 1.21 (d, J=6.4 Hz, 3H), 1.51 (m, 2H), 3.09~3.14 (m, 2H), 3.28 (d, J=4.4 Hz, 1H), 4.82 (br s, 1H), 5.03~5.09 (m, 1H), 5.14~5.17 (m, 1H), 7.22~7.55 (m, 4H)

Example 24: Synthesis of 1-(2-chlorophenyl)-(R)-1-hydroxypropyl-(R)-2-N-isopropylcarbamate (24)

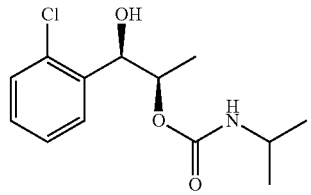 [SMILES: CC(C)NC(=O)O[C@H](C)[C@H](O)c1ccccc1Cl]

The substantially same method as described in Example 22 was conducted, except that isopropylamine was used instead of methylamine solution (CH$_3$NH$_2$ in EtOH), to obtain the title compound (0.16 g, yield 27%).

$^1$H NMR (400 MHz, CDCl$_3$) δ0.88~4.16 (m, 6H), 1.19~1.26 (m, 3H), 3.34 (s, 1H), 3.71~3.78 (m, 1H), 4.62 (br s, 1H), 5.03 (t, J=5.8 Hz, 1H), 5.13 (d, J=4.9 Hz, 1H), 7.20~7.53 (m, 4H)

Example 25: Synthesis of 1-(2-chlorophenyl)-(R)-1-hydroxypropyl-(R)-2-N-cyclopropylcarbamate (25)

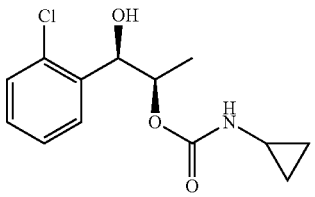 [SMILES: C[C@@H](OC(=O)NC1CC1)[C@H](O)c1ccccc1Cl]

The substantially same method as described in Example 22 was conducted, except that cyclopropylamine was used instead of methylamine solution (CH$_3$NH$_2$ in EtOH), to obtain the title compound (3.7 g, yield 60%).

$^1$H NMR (400 MHz, CDCl$_3$) δ0.49~0.54 (m, 2H), 0.74 (d, J=7.2 Hz, 2H), 1.22 (s, 3H), 2.55~2.60 (m, 1H), 3.16 (s, 1H), 5.00 (s, 1H), 5.04~5.11 (m, 1H), 5.16 (s, 1H), 7.23~7.54 (m, 4H)

Example 26: Synthesis of 1-(2-chlorophenyl)-(R)-1-hydroxypropyl-(R)-2-N-cyclohexyl carbamate (26)

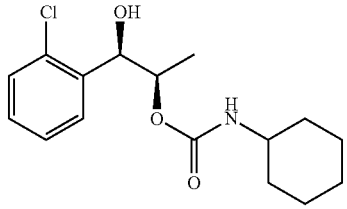 [SMILES: C[C@@H](OC(=O)NC1CCCCC1)[C@H](O)c1ccccc1Cl]

The substantially same method as described in Example 22 was conducted, except that cyclohexylamine was used instead of methylamine solution (CH$_3$NH$_2$ in EtOH), to obtain the title compound (1.9 g, yield 28%).

$^1$H NMR (400 MHz, CDCl$_3$) δ1.05~1.38 (m, 8H), 1.58~1.70 (m, 3H), 1.85~1.95 (m, 2H), 3.39~3.47 (m, 1H), 3.56 (s, 1H), 4.79 (br s, 1H), 5.01~5.07 (m, 1H), 5.14 (t, J=5.2 Hz, 1H), 7.20~7.54 (m, 4H)

Example 27: Synthesis of 1-(2-chlorophenyl)-(R)-1-hydroxypropyl-(R)-2-N-benzylcarbamate (27)

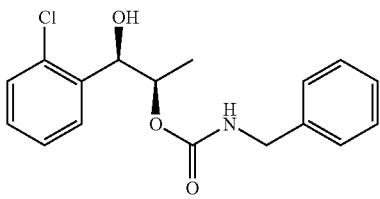 [SMILES: C[C@@H](OC(=O)NCc1ccccc1)[C@H](O)c1ccccc1Cl]

The substantially same method as described in Example 22 was conducted, except that benzylamine was used instead of methylamine solution (CH$_3$NH$_2$ in EtOH), to obtain the title compound (0.52 g, yield 19%).

$^1$H NMR (400 MHz, CDCl$_3$) δ1.25 (d, J=6 Hz, 3H), 1.64 (s, 1H), 3.13 (d, J=4.4 Hz, 1H), 4.37 (d, J=5.6 Hz, 2H), 5.12~5.19 (m, 2H), 7.23~7.55 (m, 9H)

Example 28: Synthesis of 1-(2-chlorophenyl)-(R)-1-hydroxypropyl-(R)-2-N-bicyclo[2,2,1]heptanecarbamate (28)

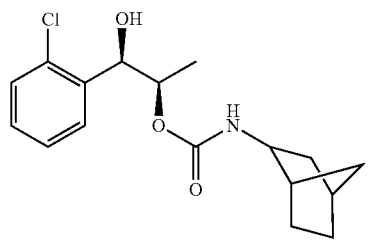 [SMILES: C[C@@H](OC(=O)NC1CC2CCC1C2)[C@H](O)c1ccccc1Cl]

The substantially same method as described in Example 22 was conducted, except that 2-aminonorbornane was used instead of methylamine solution (CH₃NH₂ in EtOH), to obtain the title compound (1.7 g, yield 20~50%).

$^1$H NMR (400 MHz, CDCl₃) δ1.08~4.35 (m, 9H), 1.65 (br s, 1H), 1.75~4.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 29: Synthesis of 1-(2-chlorophenyl)-1-hydroxypropyl-2-N-methylcarbamate (29)

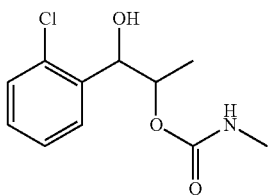 [SMILES: CNC(=O)OC(C)C(O)c1ccccc1Cl]

The substantially same method as described in Example 15 was conducted, except that 1-(2-chlorophenyl)-1,2-propanediol (Preparation example 16) was used instead of 1-(2-chlorophenyl)-(S,S)-1,2-propanediol (Preparation example 14), to obtain the title compound (2.6 g, yield 45%).

$^1$H NMR (400 MHz, CDCl₃) δ 1.21 (d, J=6 Hz, 3H), 2.81 (d, J=5 Hz, 3H), 3.14 (d, J=4 Hz, 1H), 4.72 (br s, 1H), 5.07 (dd, J=6 Hz, 1H), 5.16 (t, J=6 Hz, 1H), 7.22~7.56 (m, 4H)

Example 30: Synthesis of 1-(2-chlorophenyl)-1-hydroxypropyl-2-N-propylcarbamate (30)

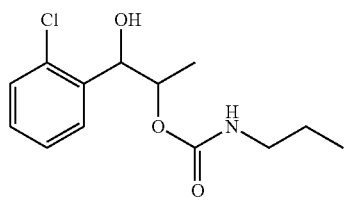 [SMILES: CCCNC(=O)OC(C)C(O)c1ccccc1Cl]

The substantially same method as described in Example 29 was conducted, except that propylamine was used instead of methylamine solution (CH₃NH₂ in EtOH), to obtain the title compound (1.0 g, yield 17%).

$^1$H NMR (400 MHz, CDCl₃) δ 0.92 (t, J=7 Hz, 3H), 1.21 (d, J=6 Hz, 3H), 1.53 (dd, J=7 Hz, 2H), 3.13 (dd, J=7 Hz, 2H), 3.28 (d, 1H), 4.82 (S, 1H), 5.06 (dd, J=7 Hz, 1H), 5.16 (t, J=5 Hz, 1H), 7.21~7.56 (m, 4H)

Example 31: Synthesis of 1-(2-chlorophenyl)-1-hydroxypropyl-2-N-isopropylcarbamate (31)

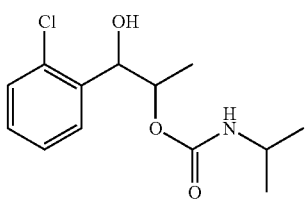 [SMILES: CC(C)NC(=O)OC(C)C(O)c1ccccc1Cl]

The substantially same method as described in Example 29 was conducted, except that isopropylamine was used instead of methylamine solution (CH₃NH₂ in EtOH), to obtain the title compound (0.54 g, yield 16%).

$^1$H NMR (400 MHz, CDCl₃) δ 1.16 (dd, J=6 Hz, 6H), 1.21 (d, J=6 Hz, 3H), 3.23 (d, J=6 Hz, 1H), 3.75~3.84 (m, 1H), 4.61 (br s, 1H), 5.06 (t, J=6 Hz, 1H), 5.16 (t, J=6 Hz, 1H), 7.22~7.56 (m, 4H)

Example 32: Synthesis of 1-(2-chlorophenyl)-1-hydroxypropyl-2-N-cyclopropylcarbamate (32)

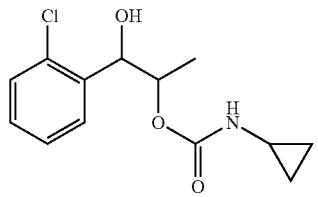 [SMILES: CC(OC(=O)NC1CC1)C(O)c1ccccc1Cl]

The substantially same method as described in Example 29 was conducted, except that cyclopropylamine was used instead of methylamine solution (CH₃NH₂ in EtOH), to obtain the title compound (1.0 g, yield 17%).

$^1$H NMR (400 MHz, CDCl₃) δ 0.50 (t, J=6 Hz, 2H), 0.77 (t, J=3 Hz, 2H), 1.12 (d, J=7 Hz, 3H), 2.53~2.59 (m, 1H), 3.22 (d, J=4 Hz, 1H), 5.08 (dd, J=6 Hz, 1H), 5.15 (S, 1H), 7.22~7.55 (m, 4H)

Example 33: Synthesis of 1-(2-chlorophenyl)-1-hydroxypropyl-2-N-cyclohexylcarbamate (33)

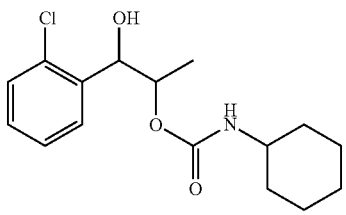 [SMILES: CC(OC(=O)NC1CCCCC1)C(O)c1ccccc1Cl]

The substantially same method as described in Example 29 was conducted, except that cyclohexylamine was used instead of methylamine solution (CH₃NH₂ in EtOH), to obtain the title compound (2.2 g, yield 33%).

$^1$H NMR (400 MHz, CDCl₃) δ 1.07~1.17 (m, 3H), 1.21 (d, J=6 Hz, 3H), 1.29~1.42 (m, 3H), 1.72 (dd, J=6 Hz, 2H), 1.92 (dd, J=6 Hz, 2H), 3.26 (d, J=4 Hz, 1H), 3.46 (t, J=4 Hz, 1H), 4.68 (d, J=6 Hz, 1H), 5.07 (dd, J=6 Hz, 1H), 5.16 (t, J=6 Hz, 1H), 7.22~7.55 (m, 4H)

Example 34: Synthesis of 1-(2-chlorophenyl)-1-hydroxypropyl-2-N-benzylcarbamate (34)

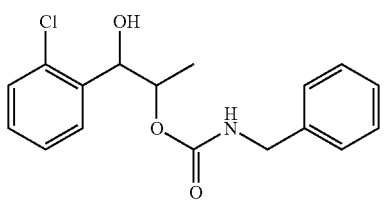 [SMILES: CC(OC(=O)NCc1ccccc1)C(O)c1ccccc1Cl]

The substantially same method as described in Example 29 was conducted, except that benzylamine was used instead of methylamine solution (CH₃NH₂ in EtOH), to obtain the title compound (1.3 g, yield 19%).

¹H NMR (400 MHz, CDCl₃) δ 1.25 (d, J=6 Hz, 3H), 3.16 (d, J=4 Hz, 1H), 4.36 (d, J=6 Hz, 2H), 5.14 (dd, J=6 Hz, 3H), 7.23~7.56 (m, 9H), yield: 19%(1.3 g)

Example 35: Synthesis of 1-(2-chlorophenyl)-1-hydroxypropyl-2-N-bicyclo[2,2,1]heptanecarbamate (35)

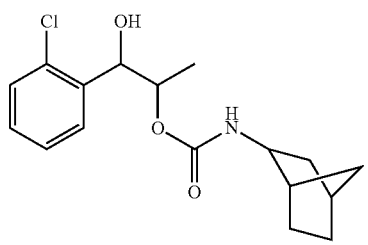 [SMILES: CC(OC(=O)NC1CC2CCC1C2)C(O)c1ccccc1Cl]

The substantially same method as described in Example 29 was conducted, except that 2-aminonorbornane was used instead of methylamine solution (CH₃NH₂ in EtOH), to obtain the title compound (1.7 g, yield 20~50%).

¹H NMR (400 MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Example 36: Synthesis of 1-(2,4-dichlorophenyl)-(S)-1-hydroxypropyl-(S)-2-carbamate (36)

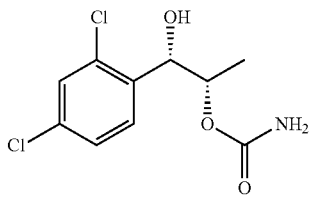 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)propane (Preparation Example 83) was used instead of 1-(2-chlorophenyl)-(S,S)-1,2-(Bis-trimethyl silanyloxy) propane (Preparation example 69) to obtain the title compound (1.8 g, yield 60~90%).

¹H NMR (400 MHz, CDCl₃) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 37: Synthesis of 1-(2,6-dichlorophenyl)-(S)-1-hydroxypropyl-(S)-2-carbamate (37)

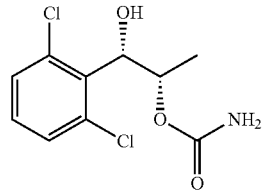 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)propane (Preparation Example 84) was used instead of 1-(2-chlorophenyl)-(S,S)-1,2-(Bis-trimethylsilanyloxy) propane (Preparation example 69) to obtain the title compound (2.6 g, yield 60~90%)

Example 38: Synthesis of 1-(2,3-dichlorophenyl)-(S)-1-hydroxypropyl-(S)-2-carbamate (38)

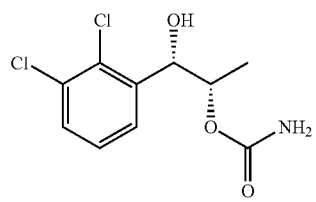 [SMILES: C[C@H](OC(N)=O)[C@@H](O)c1cccc(Cl)c1Cl]

The substantially same method as described in Example 1 was conducted, except that 1-(2,3-dichlorophenyl)-(S,S)-1,2-(Bis-trimethylsilanyloxy)propane (Preparation Example 85) was used instead of 1-(2-chlorophenyl)-(S,S)-1,2-(Bis-trimethylsilanyloxy) propane (Preparation example 69) to obtain the title compound (1.4 g, yield 60~90%)

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 39: Synthesis of 1-(2,4-dichlorophenyl)-(S)-1-hydroxybutyl-(S)-2-carbamate (39)

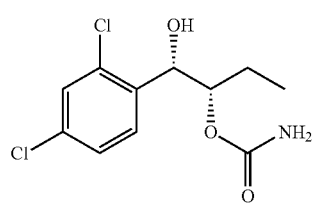

The substantially same method as described in Example 1 was conducted, except that 1-(2,4-dichlorophenyl)-(S,S)-1,2-(Bis-trimethylsilanyloxy)butane (Preparation Example 86) was used instead of 1-(2-chlorophenyl)-(S,S)-1,2-(Bis-trimethylsilanyloxy) propane (Preparation example 69) to obtain the title compound (2.3 g, yield 60~90%).

¹H NMR (400 MHz, CDCl₃) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 40: Synthesis of 1-(2,6-dichlorophenyl)-(S)-1-hydroxybutyl-(S)-2-carbamate(40)

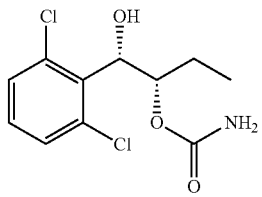 [SMILES: CC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)butane (Preparation Example 87) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 41: Synthesis of 1-(2,4-dichlorophenyl)-(S)-1-hydroxy-3-methyl-butyl-(S)-2-carbamate(41)

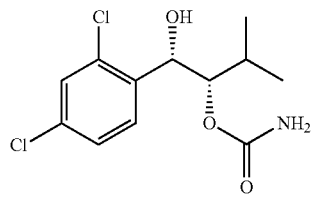 [SMILES: CC(C)[C@H](OC(N)=O)[C@@H](O)c1ccc(Cl)cc1Cl]

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 42: Synthesis of 1-(2,6-dichlorophenyl)-(S)-1-hydroxy-3-methyl-butyl-(S)-2-carbamate(42)

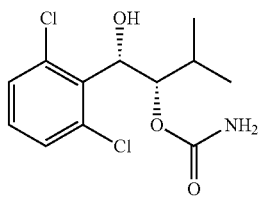 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 43: Synthesis of 1-(2,4-dichlorophenyl)-(S)-1-hydroxyhexyl-(S)-2-carbamate (43)

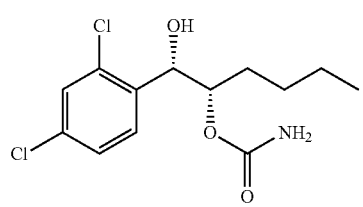 [SMILES: CCCC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR (400 MHz, CDCl$_3$) δ0.89 (t, J=3.6 Hz, 3H), 1.28~1.42 (m, 4H), 1.52~1.59 (m, 1H), 1.64~1.71 (m, 1H), 2.98 (d, 1H), 4.67 (br s, 2H), 4.96~5.00 (m, 1H), 5.17 (t, J=5.6 Hz, 1H), 7.30~7.49 (m 3H)

Example 44: Synthesis of 1-(2,6-dichlorophenyl)-(S)-1-hydroxyhexyl-(S)-2-carbamate (44)

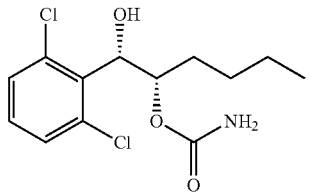 [SMILES: CCCC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy) propane (Preparation example 69) to obtain the title compound (2.1 g, yield 60~90%)

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 45: Synthesis of 1-(2,4-dichlorophenyl)-(R)-1-hydroxypropyl-(R)-2-carbamate (45)

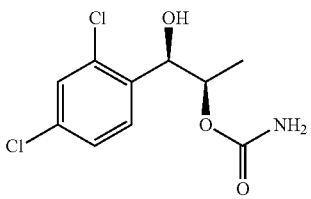 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy) propane (Preparation example 69) to obtain the title compound (1.2 g, yield 60~90%), ¹H NMR (400 MHz, CDCl₃) δ1.22 (d, J=6.4 Hz, 3H), 4.16 (br t, 1H), 4.96 (br t, 3H), 5.07 (t, J=4.8 Hz, 1H), 7.23~7.52 (m, 3H)

Example 46: Synthesis of 1-(2,6-dichlorophenyl)-(R)-1-hydroxypropyl-(R)-2-carbamate (46)

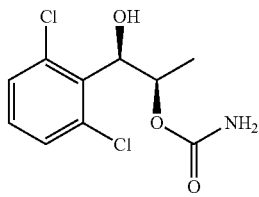 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy) propane (Preparation example 69) to obtain the title compound (1.7 g, yield 60~90%), ¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H), Example 47: Synthesis of 1-(2,3-dichlorophenyl)-(R)-1-hydroxypropyl-(R)-2-carbamate (47)

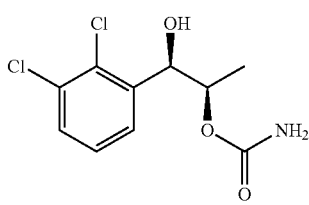 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy) propane (Preparation example 69) to obtain the title compound (2.0 g, yield 60~90%)

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 48: Synthesis of 1-(2,4-dichlorophenyl)-(R)-1-hydroxybutyl-(R)-2-carbamate(48)

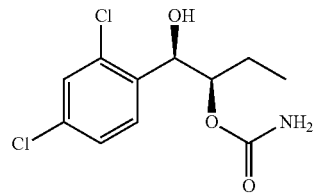 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy) propane (Preparation example 69) to obtain the title compound (2.3 g, yield 60~90%).

¹H NMR (400 MHz, CDCl₃) δ0.96 (t, J=7.4 Hz, 3H), 1.58~1.74 (m, 2H), 2.98 (d, J=5.6 Hz, 1H), 4.68 (br s, 2H), 5.59 (dt, J=5.2, 8.8 Hz, 1H), 5.19 (t, J=5.4 Hz, 1H), 7.30~7.50 (m, 3H)

Example 49: Synthesis of 1-(2,6-dichlorophenyl)-(R)-1-hydroxybutyl-(R)-2-carbamate (49)

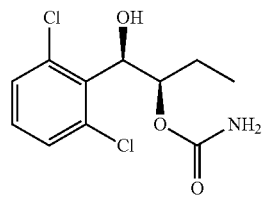 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy) propane (Preparation example 69) to obtain the title compound (2.5 g, yield 60~90%).

¹H NMR (400 MHz, CDCl₃) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 50: Synthesis of 1-(2,4-dichlorophenyl)-(R)-1-hydroxy-3-methyl-butyl-(R)-2-carbamate (50)

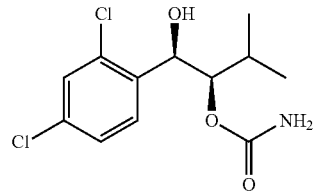 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-

(S,S)-1,2-(Bis-trimethylsilanyloxy) propane (Preparation example 69) to obtain the title compound (2.8 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 51: Synthesis of 1-(2,6-dichlorophenyl)-(R)-1-hydroxy-3-methyl-butyl-(R)-2-carbamate (51)

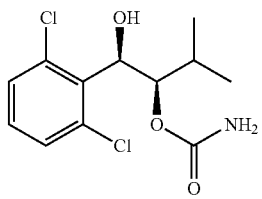 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy) propane (Preparation example 69) to obtain the title compound (2.6 g, yield 60~90%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 52: Synthesis of 1-(2,4-dichlorophenyl)-(R)-1-hydroxyhexyl-(R)-2-carbamate(52)

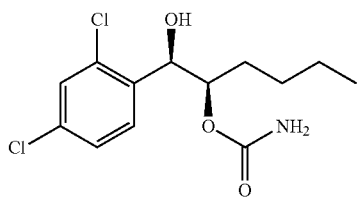 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy) propane (Preparation example 69) to obtain the title compound (2.5 g, yield 60~90%).

¹H NMR (400 MHz, CDCl₃) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Example 53: Synthesis of 1-(2,6-dichlorophenyl)-(R)-1-hydroxyhexyl-(R)-2-carbamate (53)

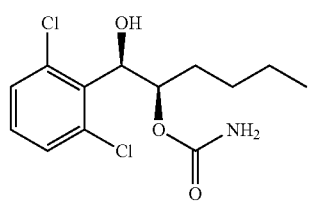 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy) propane (Preparation example 69) to obtain the title compound (2.4 g, yield 60~90%).

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 54: Synthesis of 1-(2,4-dichlorophenyl)-1-hydroxypropyl-2-carbamate (54)

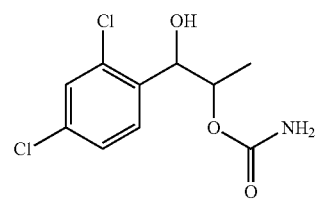 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy) propane (Preparation example 69) to obtain the title compound (1.7 g, yield 60~90%).

¹H NMR (400 MHz, CDCl₃) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 55: Synthesis of 1-(2,6-dichlorophenyl)-1-hydroxypropyl-2-carbamate (55)

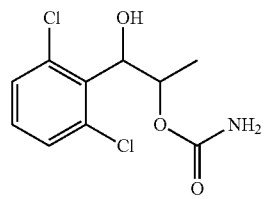 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy) propane (Preparation example 69) to obtain the title compound (2.4 g, yield 60~90%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 56: Synthesis of 1-(2,3-dichlorophenyl)-1-hydroxypropyl-2-carbamate (56)

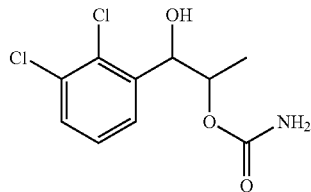 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 57: Synthesis of 1-(2,4-dichlorophenyl)-1-hydroxybutyl-2-carbamate (57)

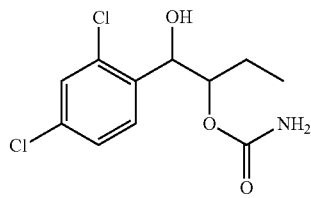 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 58: Synthesis of 1-(2,6-dichlorophenyl)-1-hydroxybutyl-2-carbamate (58)

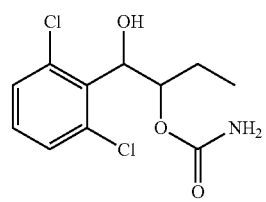 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 59: Synthesis of 1-(2,4-dichlorophenyl)-1-hydroxy-3-methyl-butyl-2-carbamate(59)

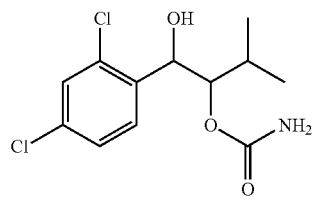 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 60: Synthesis of 1-(2,6-dichlorophenyl)-1-hydroxy-3-methyl-butyl-2-carbamate (60)

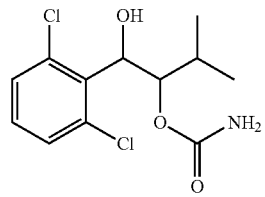 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 61: Synthesis of 1-(2,4-dichlorophenyl)-1-hydroxyhexyl-2-carbamate (61)

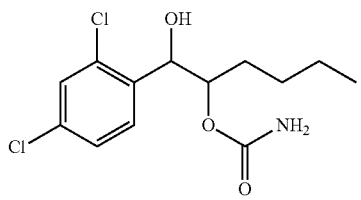 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy) propane (Preparation example 69) to obtain the title compound (2.6 g, yield 60~90%).
$^1$H NMR (400 MHz, CDCl$_3$) δ0.89 (t, J=3.6 Hz, 3H), 1.28~1.42 (m, 4H), 1.52~4.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Example 62: Synthesis of 1-(2,6-dichlorophenyl)-1-hydroxyhexyl-2-carbamate (62)

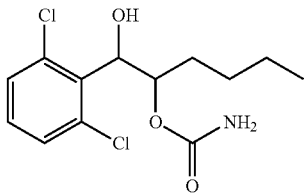 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy) propane (Preparation example 69) to obtain the title compound (2.5 g, yield 60~90%).
$^1$H NMR (400 MHz, CDCl$_3$) δ0.84 (t, J=7.0 Hz, 3H), 1.20~4.35 (m, 4H), 1.36~1.41 (m, 1H), 1.59~4.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 63: Synthesis of 1-(2-fluorophenyl)-(S)-1-hydroxypropyl-(S)-2-carbamate (63)

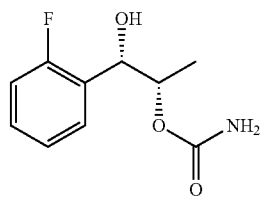

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy) propane (Preparation example 69) to obtain the title compound (1.8 g, yield 60~90%).
$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Example 64: Synthesis of 1-(2-fluorophenyl)-(R)-1-hydroxypropyl-(R)-2-carbamate (64)

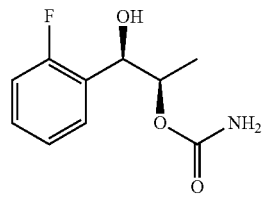

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy) propane (Preparation example 69) to obtain the title compound (1.6 g, yield 60~90%).
$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Example 65: Synthesis of 1-(2-iodophenyl)-(S)-1-hydroxypropyl-(S)-2-carbamate (65)

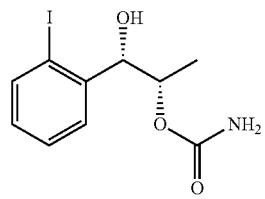

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy) propane (Preparation example 69) to obtain the title compound (2.2 g, yield 60~90%).
$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Example 66: Synthesis of 1-(2-iodophenyl)-(R)-1-hydroxypropyl-(R)-2-carbamate (66)

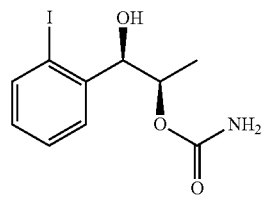

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400 MHz, CDCl$_3$) δ1.27 (d, J=6.4 Hz, 3H), 2.95 (d, J=3.6 Hz, 1H), 4.73 (br s, 2H), 5.01~5.11 (m, 2H), 7.01~7.86 (m, 4H)

Example 67: Synthesis of 1-(2-iodophenyl)-(S)-1-hydroxybutyl-(S)-2-carbamate (67)

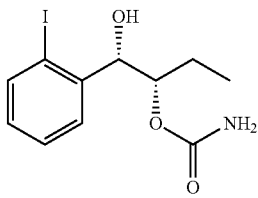 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Example 68: Synthesis of 1-(2-chlorophenyl)-(S)-2-hydroxypropyl-(S)-1-carbamate (68)

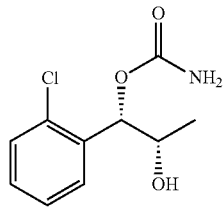

1-(2-chlorophenyl)-(S,S)-1,2-propanediol (2.33 g, Preparation example 14) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH$_4$OH, 4 ml) was added thereto. When the reaction was completed, the obtained product was washed with 1M HCl solution and ethylacetate (EA). The separated organic layer was dehydrated with anhydrous magnesium sulfate (MgSO$_4$), filtrated, and concentrated under reduced pressure. The concentrated residue was purified by a silica gel column chromatography, to obtain the title compound (0.28 g, yield 10~30%).

$^1$H NMR (400 MHz, CDCl$_3$) δ1.24 (d, J=6.8 Hz, 3H), 2.13 (d, J=4.4 Hz, 1H), 4.12~4.16 (m, 1H), 4.85 (br s, 2H), 5.98 (d, J=5.6 Hz, 1H), 7.24~7.43 (m, 4H)

Example 69: Synthesis of 1-(2-chlorophenyl)-(R)-2-hydroxypropyl-(R)-1-carbamate (69)

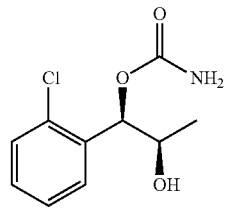

The substantially same method as described in Example 68 was conducted, except that 1-(2-chlorophenyl)-(R,R)-1,2-propanediol (Preparation Example 15) was used instead of 1-(2-chlorophenyl)-(S,S)-1,2-propanediol (Preparation example 14) to obtain the title compound (0.77 g, yield 16%).

$^1$H NMR (400 MHz, CDCl$_3$) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Example 70: Synthesis of 1-(2-chlorophenyl)-2-hydroxypropyl-1-carbamate (70)

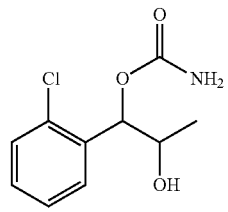

The substantially same method as described in Example 68 was conducted, except that 1-(2-chlorophenyl)-(R,R)-1,2-propanediol (Preparation Example 16) was used instead of 1-(2-chlorophenyl)-(S,S)-1,2-propanediol (Preparation example 14) to obtain the title compound (0.16 g, yield 10~30%).

$^1$H NMR (400 MHz, CDCl$_3$) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Example 71: Synthesis of 1-(2-chlorophenyl)-(S)-2-hydroxypropyl-(S)-1-N-methylcarbamate (71)

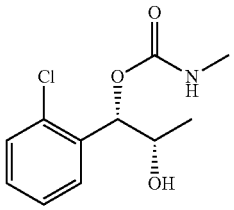 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).

¹H NMR (400 MHz, CDCl₃) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Example 72: Synthesis of 1-(2-chlorophenyl)-(R)-2-hydroxypropyl-(R)-1-N-methylcarbamate (72)

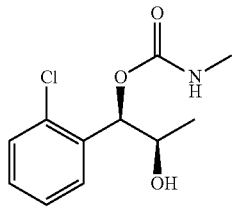 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).

¹H NMR (400 MHz, CDCl₃) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Example 73: Synthesis of 1-(2-chlorophenyl)-2-hydroxypropyl-1-N-methylcarbamate (73)

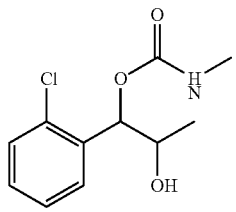 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10~30%).

¹H NMR (400 MHz, CDCl₃) δ 1.22 (d, J=6 Hz, 3H), 2.15 (d, J=4 Hz, 1H), 2.81 (d, J=5 Hz, 3H), 4.12 (dd, J=6 Hz, 1H), 4.83 (br s, 1H), 6.00 (d, J=6 Hz, 1H), 7.23~7.41 (m, 4H)

Example 74: Synthesis of 1-(2-chlorophenyl)-(S)-2-hydroxypropyl-(S)-1-N-propylcarbamate (74)

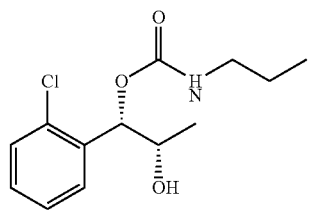

A regioisomer of monocarbamate was separated and purified by conducting the silica gel column chromatography as described in Example 16, to obtain the title compound (0.15 g, yield 10~30%).

¹H NMR (400 MHz, CDCl₃) δ 0.91 (t, J=7 Hz, 3H), 1.22 (d, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 75: Synthesis of 1-(2-chlorophenyl)-(R)-2-hydroxypropyl-(R)-1-N-propylcarbamate (75)

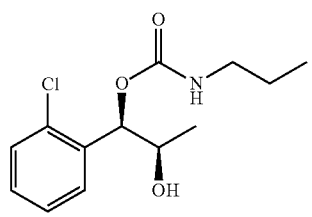 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

¹H NMR (400 MHz, CDCl₃) δ 0.91 (t, J=7 Hz, 3H), 1.22 (d, J=6 Hz, 3H), 1.52 (dd, J=7 Hz, 2H), 2.23 (d, 34 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 76: Synthesis of 1-(2-chlorophenyl)-2-hydroxypropyl-1-N-propylcarbamate (76)

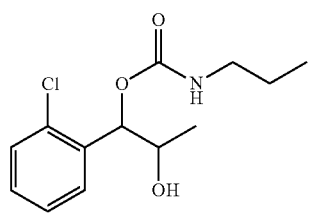 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10~30%).

¹H NMR (400 MHz, CDCl₃) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Example 77: Synthesis of 1-(2-chlorophenyl)-(S)-2-hydroxypropyl-(S)-1-N-isopropylcarbamate (77)

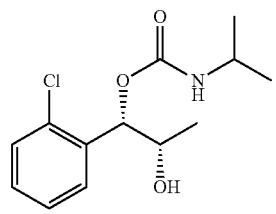 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 10~30%).
¹H NMR (400 MHz, CDCl₃) δ1.10 (d, J=6.0 Hz, 3H), 1.15~1.19 (m, 6H), 2.41 (s, 1H), 3.76~4.08 (m, 1H), 4.34 (s, 1H), 4.83 (br s 1H), 5.95 (d, J=5.3 Hz, 1H), 7.19~7.39 (m, 4H)

Example 78: Synthesis of 1-(2-chlorophenyl)-(R)-2-hydroxypropyl-(R)-1-N-isopropylcarbamate (78)

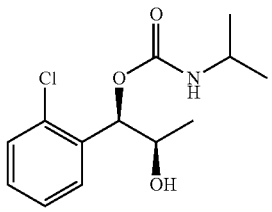 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10~30%).
¹H NMR (400 MHz, CDCl₃) δ1.13 (d, J=6 Hz, 3H), 1.20 (dd, J=9.2 Hz, 6H), 2.23 (s, 1H), 3.77~3.82 (m, 1H), 4.10 (s, 1H), 4.76 (br s, 1H), 5.98 (d, J=5.6 Hz, 1H), 7.23~7.41 (m, 4H)

Example 79: Synthesis of 1-(2-chlorophenyl)-2-hydroxypropyl-1-N-isopropylcarbamate (79)

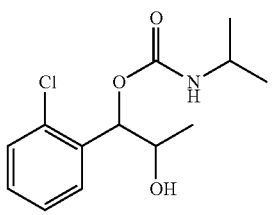 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 10~30%).
¹H NMR (400 MHz, CDCl₃) δ 1.14 (d, J=6 Hz, 3H), 1.21 (dd, J=6 Hz, 6H), 2.16 (d, J=5 Hz, 1H), 3.81 (t, J=6 Hz, 1H), 4.11 (d, J=5 Hz, 1H), 4.73 (br s, 1H), 5.98 (d, J=5 Hz, 1H), 7.24~741 (m, 4H)

Example 80: Synthesis of 1-(2-chlorophenyl)-(S)-2-hydroxypropyl-(S)-1-N-cyclopropylcarbamate (80)

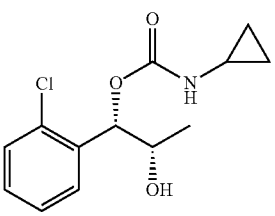 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).
¹H NMR (400 MHz, CDCl₃) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Example 81: Synthesis of 1-(2-chlorophenyl)-(R)-2-hydroxypropyl-(R)-1-N-cyclopropylcarbamate (81)

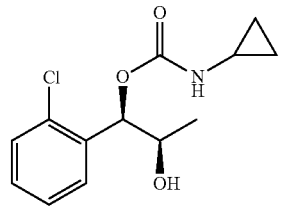 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).
¹H NMR (400 MHz, CDCl₃) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Example 82: Synthesis of 1-(2-chlorophenyl)-2-hydroxypropyl-1-N-cyclopropylcarbamate (82)

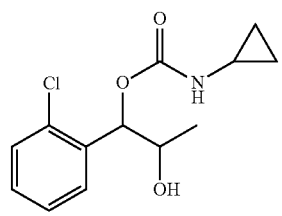 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).
¹H NMR (400 MHz, CDCl₃) δ 0.71 (s, 2H), 1.19 (d, J=6 Hz, 3H), 2.45 (S, 1H), 2.57 (S, 1H), 4.08~4.12 (m, 1H), 5.26 (s, 1H), 5.97 (d, J=4 Hz, 1H), 7.22~7.54 (m, 4H)

Example 83: Synthesis of 1-(2-chlorophenyl)-(S)-2-hydroxypropyl-(S)-1-N-cyclohexylcarbamate (83)

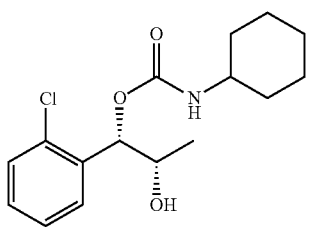 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).

¹H NMR (400 MHz, CDCl₃) δ1.10~1.39 (m, 7H), 1.61 (s, 3H), 1.71~4.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Example 84: Synthesis of 1-(2-chlorophenyl)-(R)-2-hydroxypropyl-(R)-1-N-cyclohexylcarbamate (84)

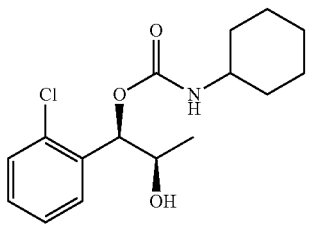 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).

¹H NMR (400 MHz, CDCl₃) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H).

Example 85: Synthesis of 1-(2-chlorophenyl)-2-hydroxypropyl-1-N-cyclohexylcarbamate (85)

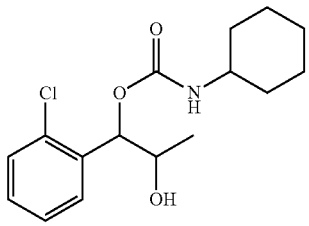 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).

¹H NMR (400 MHz, CDCl₃) δ 1.12~1.19 (m, 3H), 1.22 (d, J=6 Hz, 3H), 1.27~1.37 (m, 1H), 1.71 (t, J=6 Hz, 2H), 1.86~1.88 (m, 1H), 1.97~2.00 (m, 1H), 2.18 (d, J=4 Hz, 1H), 3.47 (S, 1H), 4.12 (t, J=6 Hz, 1H), 4.78 (S, 1H), 5.97 (d, J=6 Hz, 1H), 7.23~7.40 (m, 4H)

Example 86: Synthesis of 1-(2-chlorophenyl)-(S)-2-hydroxypropyl-(S)-1-N-benzylcarbamate (86)

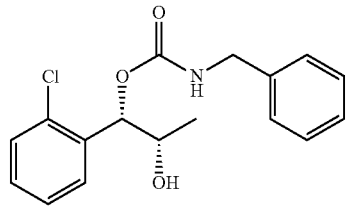 [SMILES: C[C@H](O)[C@@H](OC(=O)NCc1ccccc1)c1ccccc1Cl]

A regioisomer of monocarbamate was separated and purified by conducting the silica gel column chromatography as described in Example 20, to obtain the title compound (0.19 g, yield 10~30%).

¹H NMR (400 MHz, CDCl₃) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Example 87: Synthesis of 1-(2-chlorophenyl)-(R)-2-hydroxypropyl-(R)-1-N-benzylcarbamate (87)

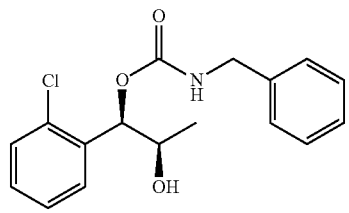 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

¹H NMR (400 MHz, CDCl₃) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Example 88: Synthesis of 1-(2-chlorophenyl)-2-hydroxypropyl-1-N-benzylcarbamate(88)

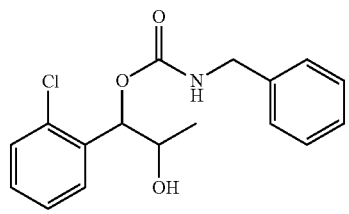 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

¹H NMR (400 MHz, CDCl₃) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Example 89: Synthesis of 1-(2,4-dichlorophenyl)-(S)-2-hydroxypropyl-(S)-1-carbamate (89)

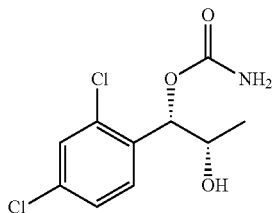 [SMILES: C[C@H](O)[C@@H](OC(N)=O)c1ccc(Cl)cc1Cl]

The substantially same method as described in Example 68 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14), to obtain the title compound (0.05 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30 (d, J=8.4 Hz, 1H), 7.39 (d, J=2.0 Hz, 2H), 7.50 (dd, J=8.4 Hz, 2.0 Hz, 1H)

Example 90: Synthesis of 1-(2,6-dichlorophenyl)-(S)-2-hydroxypropyl-(S)-1-carbamate (90)

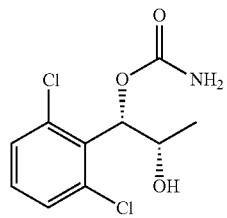 [SMILES: C[C@H](O)[C@@H](OC(N)=O)c1c(Cl)cccc1Cl]

The substantially same method as described in Example 68 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14), to obtain the title compound (0.07 g, yield 24%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Example 91: Synthesis of 1-(2,3-dichlorophenyl)-(S)-2-hydroxypropyl-(S)-1-carbamate (91)

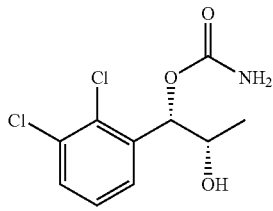 [SMILES: C[C@H](O)[C@@H](OC(N)=O)c1cccc(Cl)c1Cl]

The substantially same method as described in Example 68 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14), to obtain the title compound (0.08 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 92: Synthesis of 1-(2,4-dichlorophenyl)-(S)-2-hydroxybutyl-(S)-1-carbamate (92)

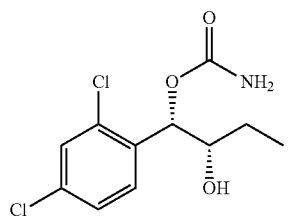 [SMILES: CC[C@H](O)[C@@H](OC(N)=O)c1ccc(Cl)cc1Cl]

The substantially same method as described in Example 68 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14), to obtain the title compound (0.07 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Example 93: Synthesis of 1-(2,6-dichlorophenyl)-(S)-2-hydroxybutyl-(S)-1-carbamate (93)

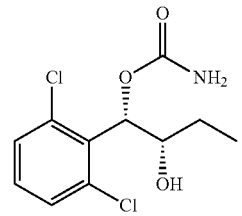

The substantially same method as described in Example 68 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14), to obtain the title compound (0.11 g, yield 29%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Example 94: Synthesis of 1-(2,4-dichlorophenyl)-(S)-2-hydroxy-3-methyl-butyl-(S)-1-carbamate (94)

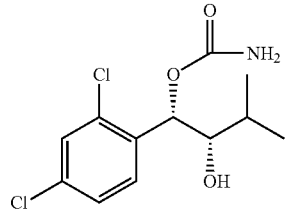 [SMILES: CC(C)[C@H](O)[C@@H](OC(N)=O)c1ccc(Cl)cc1Cl]

The substantially same method as described in Example 68 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14), to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Example 95: Synthesis of 1-(2,6-dichlorophenyl)-(S)-2-hydroxy-3-methyl-butyl-(S)-1-carbamate (95)

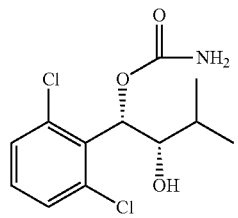

The substantially same method as described in Example 68 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14), to obtain the title compound (0.03 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Example 96: Synthesis of 1-(2,4-dichlorophenyl)-(S)-2-hydroxyhexyl-(S)-1-carbamate (96)

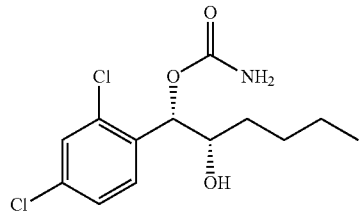

The substantially same method as described in Example 68 was conducted, except that 1-(2,4-dichlorophenyl)-(S,S)-1,2-hexanediol (Preparation example 35) was used instead of 1-(2-chlorophenyl)-(S,S)-1,2-propanediol (Preparation example 14), to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Example 97: Synthesis of 1-(2,6-dichlorophenyl)-(S)-2-hydroxyhexyl-(S)-1-carbamate (97)

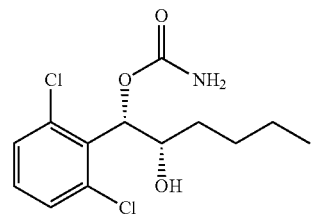

The substantially same method as described in Example 68 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14), to obtain the title compound (0.06 g, yield 29%).

$^1$H NMR (400 MHz, CDCl$_3$) δ0.85 (t, J=7.2 Hz, 3H), 1.18~4.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Example 98: Synthesis of 1-(2,4-dichlorophenyl)-(R)-2-hydroxypropyl-(R)-1-carbamate (98)

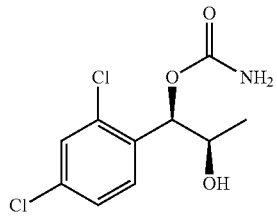 [SMILES: C[C@@H](O)[C@H](OC(N)=O)c1ccc(Cl)cc1Cl]

The substantially same method as described in Example 68 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14), to obtain the title compound (0.04 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Example 99: Synthesis of 1-(2,6-dichlorophenyl)-(R)-2-hydroxypropyl-(R)-1-carbamate (99)

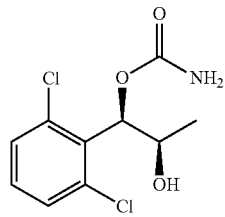 [SMILES: C[C@@H](O)[C@H](OC(N)=O)c1c(Cl)cccc1Cl]

The substantially same method as described in Example 68 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14), to obtain the title compound (0.09 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Example 100: Synthesis of 1-(2,3-dichlorophenyl)-(R)-2-hydroxypropyl-(R)-1-carbamate (100)

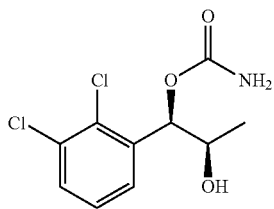 [SMILES: C[C@@H](O)[C@H](OC(N)=O)c1cccc(Cl)c1Cl]

The substantially same method as described in Example 68 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14), to obtain the title compound (0.25 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 101: Synthesis of 1-(2,4-dichlorophenyl)-(R)-2-hydroxybutyl-(R)-1-carbamate (101)

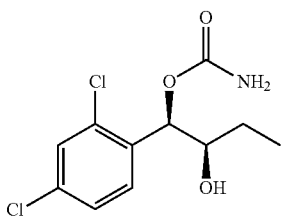 [SMILES: CC[C@@H](O)[C@H](OC(N)=O)c1ccc(Cl)cc1Cl]

The substantially same method as described in Example 68 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14), to obtain the title compound (0.08 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Example 102: Synthesis of 1-(2,6-dichlorophenyl)-(R)-2-hydroxybutyl-(R)-1-carbamate (102)

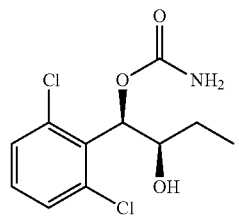 [SMILES: CC[C@@H](O)[C@H](OC(N)=O)c1c(Cl)cccc1Cl]

The substantially same method as described in Example 68 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14), to obtain the title compound (0.09 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Example 103: Synthesis of 1-(2,4-dichlorophenyl)-(R)-2-hydroxy-3-methyl-butyl-(R)-1-carbamate (103)

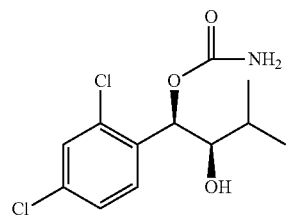 [SMILES: CC(C)[C@@H](O)[C@H](OC(N)=O)c1ccc(Cl)cc1Cl]

The substantially same method as described in Example 68 was conducted, except that 1-(2,4-dichlorophenyl)-3-methyl-(R,R)-1,2-propanediol (Preparation example 33) was used instead of 1-(2-chlorophenyl)-(S,S)-1,2-propanediol (Preparation example 14), to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Example 104: Synthesis of 1-(2,6-dichlorophenyl)-(R)-2-hydroxy-3-methyl-butyl-(R)-1-carbamate (104)

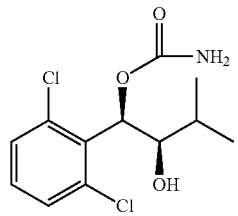 [SMILES: CC(C)[C@@H](O)[C@H](OC(N)=O)c1c(Cl)cccc1Cl]

The substantially same method as described in Example 68 was conducted, except that 1-(2,6-dichlorophenyl)-3-methyl-(R,R)-1,2-propanediol (Preparation example 45) was used instead of 1-(2-chlorophenyl)-(S,S)-1,2-propanediol (Preparation example 14), to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Example 105: Synthesis of 1-(2,4-dichlorophenyl)-(R)-2-hydroxyhexyl-(R)-1-carbamate (105)

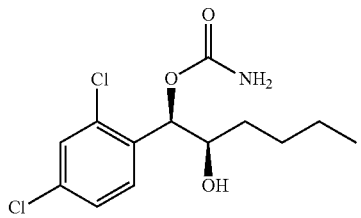 [SMILES: CCCC[C@@H](O)[C@H](OC(N)=O)c1ccc(Cl)cc1Cl]

The substantially same method as described in Example 68 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14), to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Example 106: Synthesis of 1-(2,6-dichlorophenyl)-(R)-2-hydroxyhexyl-(R)-1-carbamate (106)

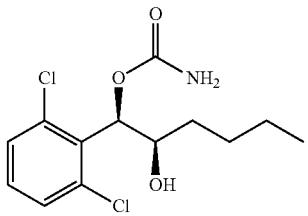 [SMILES: CCCC[C@@H](O)[C@H](OC(N)=O)c1c(Cl)cccc1Cl]

The substantially same method as described in Example 68 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14), to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, 1H), 4.45~4.50 (m, 1H), 4.76 (br s, 2H), 6.21 (d, J=8.4 Hz, 1H), 7.16~7.34 (m, 3H)

Example 107: Synthesis of 1-(2,4-dichlorophenyl)-2-hydroxypropyl-1-carbamate (107)

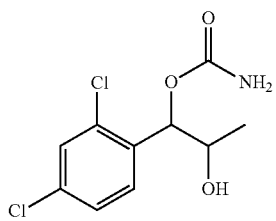 [SMILES: CC(O)C(OC(N)=O)c1ccc(Cl)cc1Cl]

The substantially same method as described in Example 68 was conducted, except that 1-(2,4-dichlorophenyl)-1,2-propanediol (Preparation example 28) was used instead of 1-(2-chlorophenyl)-(S,S)-1,2-propanediol (Preparation example 14), to obtain the title compound (0.05 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Example 108: Synthesis of 1-(2,6-dichlorophenyl)-2-hydroxypropyl-1-carbamate (108)

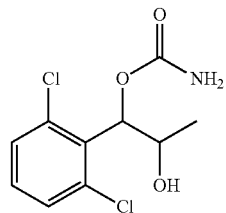 [SMILES: CC(O)C(OC(N)=O)c1c(Cl)cccc1Cl]

The substantially same method as described in Example 68 was conducted, except that 1-(2,6-dichlorophenyl)-1,2-propanediol (Preparation example 40) was used instead of 1-(2-chlorophenyl)-(S,S)-1,2-propanediol (Preparation example 14), to obtain the title compound (0.06 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Example 109: Synthesis of 1-(2,3-dichlorophenyl)-2-hydroxypropyl-1-carbamate (109)

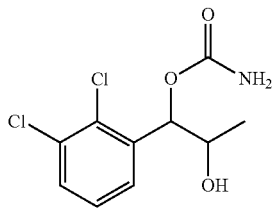 [SMILES: CC(O)C(OC(N)=O)c1cccc(Cl)c1Cl]

The substantially same method as described in Example 68 was conducted, except that 1-(2,3-dichlorophenyl)-1,2-propanediol (Preparation example 59) was used instead of 1-(2-chlorophenyl)-(S,S)-1,2-propanediol (Preparation example 14), to obtain the title compound (0.02 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 110: Synthesis of 1-(2,4-dichlorophenyl)-2-hydroxybutyl-1-carbamate (110)

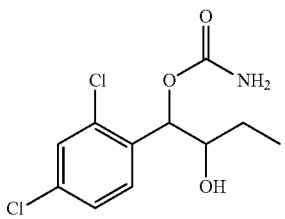 [SMILES: CCC(O)C(OC(N)=O)c1ccc(Cl)cc1Cl]

The substantially same method as described in Example 68 was conducted, except that 1-(2,4-dichlorophenyl)-1,2-butanediol (Preparation example 31) was used instead of 1-(2-chlorophenyl)-(S,S)-1,2-propanediol (Preparation example 14), to obtain the title compound (0.07 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Example 111: Synthesis of 1-(2,6-dichlorophenyl)-2-hydroxybutyl-1-carbamate (111)

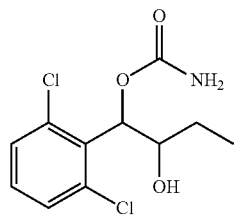 [SMILES: CCC(O)C(OC(N)=O)c1c(Cl)cccc1Cl]

The substantially same method as described in Example 68 was conducted, except that 1-(2,6-dichlorophenyl)-1,2-butanediol (Preparation example 43) was used instead of 1-(2-chlorophenyl)-(S,S)-1,2-propanediol (Preparation example 14), to obtain the title compound (0.10 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Example 112: Synthesis of 1-(2,4-dichlorophenyl)-2-hydroxy-3-methyl-butyl-1-carbamate (112)

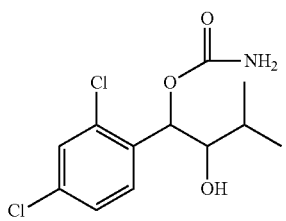 [SMILES: CC(C)C(O)C(OC(N)=O)c1ccc(Cl)cc1Cl]

The substantially same method as described in Example 68 was conducted, except that 1-(2,4-dichlorophenyl)-3-methyl-1,2-propanediol (Preparation example 34) was used instead of 1-(2-chlorophenyl)-(S,S)-1,2-propanediol (Preparation example 14), to obtain the title compound (0.04 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Example 113: Synthesis of 1-(2,6-dichlorophenyl)-2-hydroxy-3-methyl-butyl-1-carbamate (113)

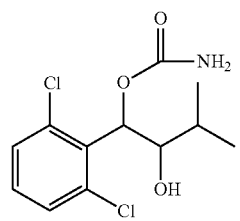 [SMILES: CC(C)C(O)C(OC(N)=O)c1c(Cl)cccc1Cl]

The substantially same method as described in Example 68 was conducted, except that 1-(2,6-dichlorophenyl)-3-methyl-1,2-propanediol (Preparation example 46) was used instead of 1-(2-chlorophenyl)-(S,S)-1,2-propanediol (Preparation example 14), to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Example 114: Synthesis of 1-(2,4-dichlorophenyl)-2-hydroxyhexyl-1-carbamate (114)

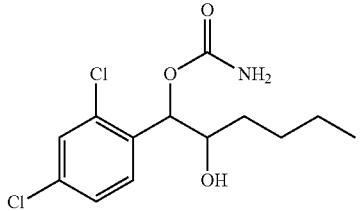 [SMILES: CCCCC(O)C(OC(N)=O)c1ccc(Cl)cc1Cl]

The substantially same method as described in Example 68 was conducted, except that 1-(2,4-dichlorophenyl)-1,2-hexanediol (Preparation example 37) was used instead of 1-(2-chlorophenyl)-(S,S)-1,2-propanediol (Preparation example 14), to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Example 115: Synthesis of 1-(2,6-dichlorophenyl)-2-hydroxyhexyl-1-carbamate (115)

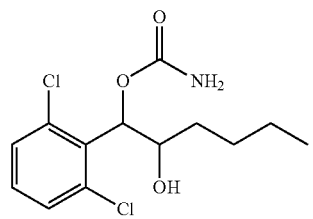 [SMILES: CCCCC(O)C(OC(N)=O)c1c(Cl)cccc1Cl]

The substantially same method as described in Example 68 was conducted, except that 1-(2,6-dichlorophenyl)-1,2-hexanediol (Preparation example 49) was used instead of 1-(2-chlorophenyl)-(S,S)-1,2-propanediol (Preparation example 14), to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

TABLE 1

Compounds 1 to 67 having the structure of Chemical Formula 1 where 'R$^7$' is a carbamoyl derivative and 'R$^6$' is H

| No. | R$^1$-R$^5$ | n (position) | 1$^{st}$ Chiral | 2$^{nd}$ Chiral | R$^8$ | R$^7$ = carbamoyl derivative, A$^1$= | R$^6$ = H |
|---|---|---|---|---|---|---|---|
| 1 | Cl | 1(2-) | S | S | Me | H | H |
| 2 | Cl | 1(2-) | R | R | Me | H | H |
| 3 | Cl | 1(2-) | Rac. | Rac. | Me | H | H |
| 4 | Cl | 1(2-) | S | R | Me | H | H |
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac, | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |

TABLE 1-continued

Compounds 1 to 67 having the structure of Chemical Formula 1 where 'R⁷' is a carbamoyl derivative and 'R⁶' is H

| No. | $R^1$-$R^5$ | n (position) | $1^{st}$ Chiral | $2^{nd}$ Chiral | $R^8$ | $R^7$ = carbamoyl derivative, $A^1$= | $R^6$ = H |
|---|---|---|---|---|---|---|---|
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2,4-) | R | R | Isopropyl | H | H |
| 51 | Cl | 2(2,6-) | R | R | Isopropyl | H | H |
| 52 | Cl | 2(2,4-) | R | R | butyl | H | H |
| 53 | Cl | 2(2,6-) | R | R | butyl | H | H |
| 54 | Cl | 2(2,4-) | Rac, | Rac. | Me | H | H |
| 55 | Cl | 2(2,6-) | Rac, | Rac. | Me | H | H |
| 56 | Cl | 2(2,3-) | Rac, | Rac. | Me | H | H |
| 57 | Cl | 2(2,4-) | Rac, | Rac. | Et | H | H |
| 58 | Cl | 2(2,6-) | Rac, | Rac. | Et | H | H |
| 59 | Cl | 2(2,4-) | Rac, | Rac. | Isopropyl | H | H |
| 60 | Cl | 2(2,6-) | Rac, | Rac. | Isopropyl | H | H |
| 61 | Cl | 2(2,4-) | Rac, | Rac. | butyl | H | H |
| 62 | Cl | 2(2,6-) | Rac, | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 2

Compounds 68 to 115 having the structure of Chemical Formula 1 where 'R⁷' is H and 'R⁶' is a carbamoyl derivative

| No. | $R^1$-$R^5$ | n (position) | $1^{st}$ Chiral | $2^{nd}$ Chiral | $R^8$ | $R^7$ = H | $R^6$ = carbamoyl derivative, $A^1$= |
|---|---|---|---|---|---|---|---|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |

TABLE 2-continued

Compounds 68 to 115 having the structure of Chemical Formula 1 where 'R$^7$' is H and 'R$^6$' is a carbamoyl derivative

| No. | R$^1$-R$^5$ | n (position) | 1$^{st}$ Chiral | 2$^{nd}$ Chiral | R$^8$ | R$^7$ = H | R$^6$ = carbamoyl derivative, A$^1$= |
|---|---|---|---|---|---|---|---|
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

Anti-Anxiety and Depression Activity Using PTZ

In this experiment, administered intraperitoneally to test animals (Mouse; ICR, and Rats; SD); Experimental animal, male SD rats, were purchased from OrientBio or Nara biotech, Korea, and housed 4-5 mice per a cage for 4-5 days. The range of mice body weight was used between 19 and 26 grams and range of rats body weight was used between 100 and 130 grams. After Peak time (0.5, 1, 2 and 4 hr) from the administration, from the administration, PTZ (Pentylenetetrazol) was administered subcutaneously in the concentration capable of inducing 97% intermittent convulsions (mice & rats: 90~110 mg/kg·bw, 2 µl/g). If clonic seizure was not observed for at least 3 seconds in the PTZ administered animal, it can be considered that the test compound has anti-anxiety and depression activity. The median effective dose (ED50) is determined using 6 animals per a concentration (total three different concentrations), and calculated by Litchfield and Wicoxon log-probit method which is a dose-response relationship. The obtained results are shown in following Table 3.

Neurotoxicity

The measurement of neurotoxicity of the test compounds was conducted by the method of Dunham and Miya [Dunham, N. W. and Miya, T. S. 1957. A note on a simple apparatus for detecting neurological deficit in rats and mice. J. Am. Pharm. Assoc. (Baltimore) 46: 208-209]. In the method, motor abilities of the test animals can be determined by observing whether the test animals can walk without falling from a rotator, thereby determining the value of neurotoxicity of each compound. Term "TD50" means the respective dose of the test compound at which 50% of the test animal exhibit neurotoxicity. They were pre-trained on the rotarod (Rotarod; Columbus instrument, rota-max, USA) at 6 rpm for 5 min 24 hr prior to the test. The peak time was determined by administration test material's random dose for 0.5, 1, 2, 4 hour. To evaluate the minimal neurotoxicity of the compound, the mice were placed on the Rotarod (rod circle; 3 Cm) at 6 rpm and the test animal fails to maintain walking once or more during 1 minute, it can be regarded that the test animal exhibits neurotoxicity. The obtained results are shown in following Table 3.

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

TABLE 3

Measurement results of anti-anxiety and depression activity of compounds in the test animals

| Compound (Example) No. | PTZ test (ip) | | Rats | TD50 |
|---|---|---|---|---|
| | Mice | | | |
| | ED50 (mg/kg) | Peak Time (h) | ED50 (mg/kg) | Mice (mg/kg, po) |
| 1 | 15.8 | 2 | — | 218.1 |
| 2 | 38.8 | 0.5 | 51.9 (*1) | 372.0 |
| 3 | 15.3 | 0.5 | 81.9 (*0.5) | 378.3 |
| 4 | 26.7 | 0.5 | $^b$30 (50%) | — |
| 5 | 15.0 | 0.5 | — | 275.2 |
| 6 | 17.9 | 0.5 | $^b$30 (50%) | — |
| 8 | $^a$20.4 (50%) | — | — | — |
| 9 | $^a$20.4 (33.3%) | — | — | — |
| 12 | $^a$20.4 (33.3%) | — | — | — |
| 13 | $^a$20.4 (50%) | — | — | — |
| 14 | $^a$20.4 (16.7%) | — | — | — |
| 15 | — | — | $^b$25 (33.3%) | — |
| 16 | — | — | $^b$30 (33.3%) | — |
| 18 | — | — | $^b$30 (16.7%) | — |
| 23 | $^a$20.4 (50%) | — | — | — |
| 25 | $^a$20.4 (66.7%) | — | — | — |
| 29 | $^a$20.4 (33.3%) | — | — | — |
| 30 | $^a$20.4 (33.3%) | — | — | — |
| 31 | $^a$20.4 (83.3%) | — | — | — |
| 32 | $^a$20.4 (16.7%) | — | — | — |
| 36 | $^a$20.4 (33.3%) | — | — | — |
| 37 | 25.7 | 0.25 | $^b$30 (50%) | 131.6 |
| 38 | $^a$20.4 (50%) | — | — | — |
| 39 | 24.3 | 0.5 | — | — |
| 40 | $^a$20.4 (33.3%) | — | — | — |
| 42 | $^a$20.4 (50%) | — | — | — |
| 43 | — | — | $^b$25 (33.3%) | — |
| 44 | $^a$20.4 (33.3%) | — | — | — |
| 45 | $^a$20.4 (16.7%) | — | $^b$50 (16.7%) | — |
| 46 | $^a$20.4 (50%) | — | — | — |
| 63 | $^a$20.4 (50%) | — | — | — |
| 65 | $^a$20.4 (100%) | — | — | — |
| 67 | 23.1 | 0.5 | $^b$30 (33.3%) | — |

$^a$Injection amount (mg/kg), Protection % (Mice)/
$^b$Injection amount (mg/kg), Protection % (Rats),
*Peak Time (h)

Corneal Kindling (CK) Rat Model

Male Sprague-Dawley rats (purchased from Orient Bio Inc. Korea) of body weight 85-100 g were used for these studies. The MES test using the electroshock seizure apparatus designed by Rodent Shocker Type221 (Hugo Sachs Elektronik, Germany). The kindled rat models were electrically stimulated (8 mA, 60 Hz, 2 s, corneal electrodes) twice daily for 21 days until stage 5 seizure scored by Racine's scale (Racine, 1972) were evoked. The kindled rats were fasted and adapted to test condition, for at least 1 hour before the administration of test material. The drugs were administered orally (p.o.) in a volume of 4 μl/g body weight. The corneally kindled rat model test is a model for generalized absence seizures or bipolar disorder and identifies the compound which prevents seizure or bipolar disorder spread. The shock level was set at 8 mA, 60 Hz and the duration was set at 2 s. A drop of 0.9% saline was placed in each eye, the electrodes were placed over the eyes, and the shock was administered immediately. Pharmacological effects of the test materials were evaluated to compare the test groups (n=6) with a control group (n=6). Control group was administrated vehicle, only. The peak time was determined by administration test material's random dose for 0.5, 1, 2, 4 hour. The time that the most protect was defined peak time and ED50 was determined by other dose administration at peak time. The effective dose of compound necessary to protect against seizures to 50% of controls (ED50) was determined by log probit analysis using SPSS software program (SPSS Inc.). The obtained results are shown in following Table 4. (Reference; Ewart A. William E. Bondinell (1991)). Anticonvulsant profiles of the potent and orally active GABA uptake inhibitors SK&F 89976-A and SK&F 100330-A and four prototype antiepileptic drugs in mice and rats. *Epilepsia*, 32: 569-577./Hinko C. N., Crider A. M., Kliem M. A., Steinmiler C. L., Seo T. H., Bin Ho., Venkatarangan P., El-Assadi A. A., Chang H., Burns C. M., Tietz E. I., Andersen P. H., Klitgaard H. (1996). Anticonvulsant activity of novel derivatives of 2- and 3-pieridinecarboxylix acid in mice and rats. Neuropharmacology, 35: 1721-1735).

Hippocampal Kindling (HK) Rat Model

The hippocampal kindling model can be used to evaluate a compound's ability to affect both the expression and acquisition of focal seizures or bipolar disorder. The hippocampal kindling paradigm as described by Lothman and Williamson (1994) requires the surgical placement of bipolar electrodes in the ventral hippocampus of adult male Sprague-Dawley rats. Stage 5 seizures (Racine, 1972) are produced by using a stimulus consisting of a 50 Hz, 10 s train of 1 ms biphasic 200 uA pulses delivered every 30 min for 6 hours (12 stimulus per day) on alternating days for a total of 60 stimulations (5 stimulus days). Prior to evaluating a candidate's anticonvulsant activity, a drug free control period consisting of supramaximal stimulations is recorded to verify the stability of a stage 5 generalized seizure. A single dose of the candidate compound is then administered intraperitoneally (i.p.), 15 min following the last control stimulation. The anticonvulsant activity of the drug is assessed every 30 min for three to four hours starting 15 min after administering the test material. After each stimulation, individual Racine seizure scores and after discharge durations are recorded. In the kindling acquisition study, drugs are tested for their ability to prevent the development of the kindled state in electrode implanted rats. The candidate compound is administered during the kindling procedure. For these studies, drug is administered at a predetermined time prior to the electrical stimulus. The dosing interval and the dose of the drug are based on the treated animals are compared to those of saline-treated rats. This treatment is repeated on stimulus days two, three, four, and five. After a stimulus-free interval of one week, the effect of prior drug treatment on kindling acquisition is assessed by challenging the animal with the kindling stimulus protocol. The standardized kindling protocol is then carried out with the behavioral seizure score and after discharge duration recorded for each rat during three retest days. Saline treated rats are fully kindled at the first stimulation following the one week stimulus-free period. An active compound would be expected to lower behavioral scores and after discharge duration compared to saline control rats. The suppression or lengthening of the delay in the acquisition of the kindled response may indicate that the candidate compound can act to prevent the development of seizure and biopolar disorders. The obtained results are shown in following Table 4 (Reference; Rotheman E. W. and Williamson J. M. (1994). Closely spaced recurrent hippocampal seizures elicit two types of heightened epileptogenesis: a rapidly developing, transient kindling and a slowly developing, enduring kindling. Brain Res. 649: 71-84./Racine R. J. (1972). Modification of seizure activity by electrical stimulation: II Motor seizure. Electroenceph. Clin. Neurophysiol. 32: 281-294).

TABLE 4

Measurement results of anti-psychiatry activity of compounds in the test (Rats)

| Compound (Example) No. | CK(po) ED50 (mg/kg) | HK (ip) ED50 (mg/kg) |
| --- | --- | --- |
| 1  | 2.8 (*2 h)     | 17.6 |
| 2  | ᵃ20 (16.7%)    | —    |
| 3  | ᵃ10 (50%)      | —    |
| 4  | ᵃ30 (100%)     | —    |
| 5  | ᵃ30 (50%)      | —    |
| 6  | ᵃ10 (33.3%)    | —    |
| 9  | ᵃ30 (16.7%)    | —    |
| 36 | ᵃ30 (50%)      | —    |
| 37 | ᵃ10 (33.3%)    | —    |
| 38 | ᵃ30 (50%)      | —    |
| 39 | ᵃ25 (100%)     | —    |
| 46 | ᵃ20 (50%)      | —    |
| 63 | ᵃ20 (100%)     | —    |
| 65 | ᵃ2.8 (33.3%)   | —    |
| 67 | ᵃ30 (100%)     | —    |

ᵃInjection amount (mg/kg), Protection % (Rats),
*Peak Time

Light-Dark Choice Test

The light-dark choice test is model for anxiety-like behavior. This test is based on the innate aversion of rodents to brightly illuminated areas and on their spontaneous exploratory behaviour in response to mild stressors, i.e. novel environment and light. ICR Male mice (30-35 g) old were purchased from Samtako bio korea (Korea) and allowed to acclimate for 1 week before testing in a controlled (temperature 22±2° C., humidity 55%±5%) animal facility. At the beginning of the treatments, the bodyweight of animals was 30±3 g.

The test compounds dissolved in 30% PEG400 and prepared immediately before use and were administered i.p. in a volume of 10 ml/kg body weight 60 min before the experiments. Control groups received the corresponding vehicles. A acrylic box (45 cm×27 cm with 27 cm walls) was consisted of two chambers (white: two-thirds of the box, dark: one-third of the box) connected by an opening (7.5× 7.5 cm) located at floor level in the center of the dividing wall. Each mouse was placed in the white part of the box and allowed to freely locomote for a 5 min session. At the end of the session mice were returned to their home cages and the area was wiped clean with a 70% alcohol solution. All the experiments were videotaped. After the experiment, all video recording was analyzed. The obtained results are shown in following Table 5 (References; Bourin, M., Hascoet, M. 2003. The mouse light/dark box test. *European Journal of Pharmacology,* 463, 55-65.

Bouwknecht, J A., Paylor, R. 2002. Behavioral and physiological mouse assays for anxiety: a survey in nine mouse strains. *Behavioural Brain Research,* 136, 489-501.).

Statistical Analysis

Results are expressed as mean±standard error of the mean (SEM). Behavioral data were analyzed by two-tailed unpaired t-test. A p-value of <0.05 was taken for statistical significance (*p<0.001, p=0.001-0.01, *p=0.01-0.05). Data management and statistics were performed using Prism software for Windows version 4. (GraphPad Software, San Diego, Calif., USA).

TABLE 5

Measurement results of anti-anxiety activity of compounds in the test (Mice)

| Compound (Example) No. | Dose (mg/kg) | White box duration (sec)/5 min | |
|---|---|---|---|
| | | Treatment | Control |
| 1 | 10 | 283.9 ± 6.2*** | 180.3 ± 19.3 |
| 2 | 20 | 233.8 ± 25.5** | 113.2 ± 12.3 |
| 3 | | 208.2 ± 25.5* | |
| 4 | | 222.3 ± 23.7** | |
| 5 | | 195.9 ± 18.5** | |
| 6 | | 237.2 ± 25.5** | |
| 9 | | 225.5 ± 16.8** | |
| 13 | | 196.8 ± 8.2*** | |
| 23 | | 203.2 ± 15.7** | |
| 25 | | 157.2 ± 15.9** | |
| 31 | | 193.5 ± 13.8** | |
| 37 | | 193.8 ± 28.5** | |
| 38 | | 236.2 ± 17.8*** | |
| 39 | | 229.1 ± 22.4** | |
| 42 | | 181.3 ± 15.4** | |
| 46 | | 239.8 ± 29.1** | |
| 63 | | 221.5 ± 21.9** | |
| 65 | | 243.6 ± 23.0** | |
| 67 | | 194.6 ± 20.0** | |

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating a psychiatric disorder selected from the group consisting of depressive disorder, bipolar disorder, and anxiety disorder comprising administering a pharmaceutically effective amount of a composition comprising a compound represented by the following formula 1 or pharmaceutically acceptable salt thereof to a subject in need thereof:

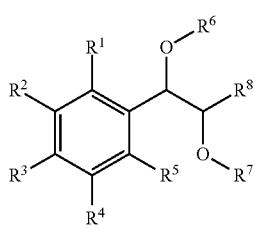

(1)

wherein $R^1$, $R^2$, $R^3$, $R^4$ and $R^5$ are each independently selected from the group consisting of hydrogen and halogen; $R^6$ is H and $R^7$ is

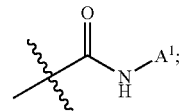

or $R^6$ is

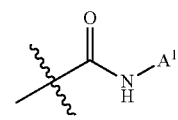

and $R^7$ is H; ($A^1$ is selected from the group consisting of hydrogen, $C_1$-$C_5$ alkyl, $C_3$-$C_8$ cycloalkyl, $C_6$-$C_{10}$ aryl, $C_1$-$C_3$ alkyl and bridged $C_6$-$C_8$ bicycloalkane); and $R^8$ is $C_1$-$C_5$ alkyl.

2. The method according to claim 1, wherein $R^1$, $R^2$, $R^3$, $R^4$ and $R^5$ are each independently selected from the group consisting of hydrogen, chlorine, fluorine and iodine.

3. The method according to claim 1, wherein the compound is selected from the group consisting of:
  (1) 1-(2-chlorophenyl)-1-hydroxypropyl-2-carbamate;
  (2) 1-(2-chlorophenyl)-1-hydroxybutyl-2-carbamate;
  (3) 1-(2-chlorophenyl)-1-hydroxy-3-methyl-butyl-2-carbamate;
  (4) 1-(2-chlorophenyl)-1-hydroxyhexyl-2-carbamate;
  (5) 1-(2-chlorophenyl)-1-hydroxypropyl-2-N-methylcarbamate;
  (6) 1-(2-chlorophenyl)-1-hydroxypropyl-2-N-propylcarbamate;
  (7) 1-(2-chlorophenyl)-1-hydroxypropyl-2-N-isopropylcarbamate;
  (8) 1-(2-chlorophenyl)-1-hydroxypropyl-2-N-cyclopropylcarbamate;
  (9) 1-(2-chlorophenyl)-1-hydroxypropyl-2-N-cyclohexylcarbamate;
  (10) 1-(2-chlorophenyl)-1-hydroxypropyl-2-N-benzylcarbamate;
  (11) 1-(2-chlorophenyl)-1-hydroxypropyl-2-N-bicyclo[2,2,1]heptanecarbamate;
  (12) 1-(2,4-dichlorophenyl)-1-hydroxypropyl-2-carbamate;
  (13) 1-(2,6-dichlorophenyl)-1-hydroxypropyl-2-carbamate;
  (14) 1-(2,4-dichlorophenyl)-1-hydroxybutyl-2-carbamate;
  (15) 1-(2,6-dichlorophenyl)-1-hydroxybutyl-2-carbamat;
  (16) 1-(2,4-dichlorophenyl)-1-hydroxy-3-methyl-butyl-2-carbamate;
  (17) 1-(2,6-dichlorophenyl)-1-hydroxy-3-methyl-butyl-2-carbamate;
  (18) 1-(2,4-dichlorophenyl)-1-hydroxyhexyl-2-carbamate;
  (19) 1-(2,6-dichlorophenyl)-1-hydroxyhexyl-2-carbamate;
  (20) 1-(2-chlorophenyl)-2-hydroxypropyl-1-carbamate;
  (21) 1-(2-chlorophenyl)-2-hydroxypropyl-1-N-methylcarbamate;

(22) 1-(2-chlorophenyl)-2-hydroxypropyl-1-N-propylcarbamate;
(23) 1-(2-chlorophenyl)-2-hydroxypropyl-1-N-isopropylcarbamate;
(24) 1-(2-chlorophenyl)-2-hydroxypropyl-1-N-cyclopropylcarbamate;
(25) 1-(2-chlorophenyl)-2-hydroxypropyl-1-N-cyclohexylcarbamate;
(26) 1-(2-chlorophenyl)-2-hydroxypropyl-1-N-benzylcarbamate;
(27) 1-(2,4-dichlorophenyl)-2-hydroxypropyl-1-carbamate;
(28) 1-(2,6-dichlorophenyl)-2-hydroxypropyl-1-carbamate;
(29) 1-(2,4-dichlorophenyl)-2-hydroxybutyl-1-carbamate;
(30) 1-(2,6-dichlorophenyl)-2-hydroxybutyl-1-carbamate;
(31) 1-(2,4-dichlorophenyl)-2-hydroxy-3-methyl-butyl-1-carbamate;
(32) 1-(2,6-dichlorophenyl)-2-hydroxy-3-methyl-butyl-1-carbamate;
(33) 1-(2,4-dichlorophenyl)-2-hydroxyhexyl-1-carbamate;
(34) 1-(2,6-dichlorophenyl)-2-hydroxyhexyl-1-carbamate;
(35) 1-(2-fluorophenyl)-1-hydroxypropyl-2-carbamate;
(36) 1-(2-iodophenyl)-1-hydroxypropyl-2-carbamate;
(37) 1-(2-iodophenyl)-1-hydroxybutyl-2-carbamate;
(38) 1-(2,3-dichlorophenyl)-1-hydroxypropyl-2-carbamate; and
(39) 1-(2,3-dichlorophenyl)-2-hydroxypropyl-1-carbamate.

4. The method according to claim 3, wherein the compound is selected from the group consisting of:
(1) 1-(2-chlorophenyl)-1-hydroxypropyl-2-carbamate;
(2) 1-(2-chlorophenyl)-1-hydroxybutyl-2-carbamate;
(4) 1-(2-chlorophenyl)-1-hydroxyhexyl-2-carbamate;
(6) 1-(2-chlorophenyl)-1-hydroxypropyl-2-N-propylcarbamate;
(8) 1-(2-chlorophenyl)-1-hydroxypropyl-2-N-cyclopropylcarbamate;
(12) 1-(2,4-dichlorophenyl)-1-hydroxypropyl-2-carbamate;
(13) 1-(2,6-dichlorophenyl)-1-hydroxypropyl-2-carbamate;
(14) 1-(2,4-dichlorophenyl)-1-hydroxybutyl-2-carbamate;
(17) 1-(2,6-dichlorophenyl)-1-hydroxy-3-methyl-butyl-2-carbamate;
(35) 1-(2-fluorophenyl)-1-hydroxypropyl-2-carbamate;
(36) 1-(2-iodophenyl)-1-hydroxypropyl-2-carbamate;
(37) 1-(2-iodophenyl)-1-hydroxybutyl-2-carbamate; and
(38) 1-(2,3-dichlorophenyl)-1-hydroxypropyl-2-carbamate.

5. The method according to claim 1, wherein the compound is in the form of racemate, enantiomer, diastereomer, a mixture of enantiomer or a mixture of diastereomer.

6. The method according to claim 1, wherein the pharmaceutically acceptable salt is produced by reacting the compound with an inorganic acid, an organic acid, an amino acid, sulfonic acid, an alkali metal or ammonium ion.

* * * * *